United States Patent [19]
Adair et al.

[11] Patent Number: 5,877,293
[45] Date of Patent: Mar. 2, 1999

[54] CDR GRAFTED ANTI-CEA ANTIBODIES AND THEIR PRODUCTION

[75] Inventors: John Robert Adair, High Wycombe; Mark William Bodmer, South Hinksey; Andrew Mountain, Wokingham; Raymond John Owens, Henley-on-Thames, all of United Kingdom

[73] Assignee: Celltech Therapeutics Limited, Slough, United Kingdom

[21] Appl. No.: 449,287

[22] Filed: May 24, 1995

Related U.S. Application Data

[63] Continuation of Ser. No. 154,389, Nov. 17, 1993, abandoned, which is a continuation of Ser. No. 847,995, Apr. 21, 1992, abandoned which is a continuation of PCT/GB90/01108 Jul. 5, 1991.

[30] Foreign Application Priority Data

Jul. 5, 1990 [GB] United Kingdom ............ 9014932

[51] Int. Cl.$^6$ ............ C07K 19/00; C07K 16/30
[52] U.S. Cl. ............ 530/387.3; 536/23.53; 530/388.8
[58] Field of Search ............ 435/70.21, 69.7, 435/69.6, 69.1, 122.2, 240.27, 252.3, 320.1, 252.33; 436/2.1, 501, 536, 5.17, 548; 530/387.3, 387.7, 388.8, 388.85, 391.3, 866, 869; 536/23.53

[56] References Cited

U.S. PATENT DOCUMENTS 5,530,101  6/1996  Queen et al. .................. 530/387.3

FOREIGN PATENT DOCUMENTS 0239400  9/1987  European Pat. Off. ........ C12N 15/00
0323805  7/1989  European Pat. Off. ........ C12P 21/00
0323806  7/1989  European Pat. Off. ........ C12N 15/00

OTHER PUBLICATIONS

Washington Post "Colon Cancer Test Found To Be Flawed" Aug. 25, 1993.

Curti: Crit. Rev. Onc/Hemat. 14:29–39 1993.

Queen et al PNAS 86:10029–10033 1989.

Biechmann et al Nature 332:323–327 1988.

HAMS TibTech 11:42–44 1993.

Waldmann Science 252:1657–1662 1991.

*Primary Examiner*—Frank C. Eisenschenk
*Attorney, Agent, or Firm*—Woodcock Washburn Kurtz Mackiewicz & Norris, LLP

[57] ABSTRACT

The present invention provides humanized antibody molecules (HAMs) having specificity for carcinoembryonic antigen (CEA) and having an antigen binding site wherein at least one of the complementarity determining regions (CDRs) of the variable domains is derived from the mouse monoclonal antibody A5B7 (A5B7 MAB) and the remaining immunoglobulin-derived parts of the HAM are derived from a human immunoglobulin. The HAMs may be chimeric humanized antibodies or CDR-grafted humanized antibodies and are preferably produced by recombinant DNA techniques. The HAMs are useful for in vivo diagnosis and therapy.

9 Claims, 31 Drawing Sheets

FIG. 1 A5B7: LIGHT CHAIN SEQUENCE
DNA AND PROTEIN SEQUENCE OF THE VI DOMAIN

```
ATGGATTTTCAAGTGCAGATTTTCAGCTTCCTGCTAATCAGTGCTTCAGTCATAATGTCC
 M  D  F  Q  V  Q  I  F  S  F  L  L  I  S  A  S  V  I  M  S
➤
AGAGGACAAACTGTTCTCTCCCAGTCTCCAGCAATCCTGTCTGCATCTCCAGGGGAGAAG
 R  G  Q  T  V  L  S  Q  S  P  A  I  L  S  A  S  P  G  E  K

GTCACAATGACTTGCAGGGCCAGCTCAAGTGTAACTTACATTCACTGGTACCAGCAGAAG
 V  T  M  T  C  R  A  S  S  S  V  T  Y  I  H  W  Y  Q  Q  K

CCAGGATCCTCCCCCAAATCCTGGATTTATGCCACATCCAACCTGGCTTCTGGAGTCCCT
 P  G  S  S  P  K  S  W  I  Y  A  T  S  N  L  A  S  G  V  P

GCTCGGCTTCAGTGGCAGTGGGTCTGGGACCCTCTTACTCTCTCACAATCAGCAGAGTGGAG
 A  R  F  S  G  S  G  S  G  T  S  Y  S  L  T  I  S  R  V  E

GCTGAAGATGCTGCCACTTATTACTGCCAACATTGGAGTAGTAAACCACCGACGTTCGG
 A  E  D  A  A  T  Y  Y  C  Q  H  W  S  S  K  P  P  T  F  G

GGAGGCACCAAGCTGGAAATCAAACGG
 G  G  T  K  L  E  I  K  R
```

A

FIG. 1(contd.) A5B7: HEAVY CHAIN SEQUENCE
DNA AND PROTEIN SEQUENCE OF THE Vh DOMAIN

```
ATGAAGTTGTGGCTGAACTGGATTTCCTTGTAACACTTTAAATGTATCCAGTGTGAG
 M  K  L  W  L  N  W  I  F  L  V  T  L  L  N  G  I  Q  C  E

GTGAAGCTGGTGGAGTCTGGGGGAGGCTTGGTACAGCCTGGGGGTTCTCTGAGACTCTCC
 V  K  L  V  E  S  G  G  G  L  V  Q  P  G  G  S  L  R  L  S

TGTGCAACTTCTGGGTTCACCTTCACTGATTACTACATGAACTGGGTCCGCCAGCCTCCA
 C  A  T  S  G  F  T  F  T  D  Y  Y  M  N  W  V  R  Q  P  P

GGAAAGGCACTTGAGTGGTTGGGTTTTATTGGAAACAAAGCTAATGGTTACACAACAGAG
 G  K  A  L  E  W  L  G  F  I  G  N  K  A  N  G  Y  T  T  E

TACAGTGCATCTGTGAAGGGTCGGTTCACCATCTCCAGAGATAAATCCCAAGCATCCTC
 Y  S  A  S  V  K  G  R  F  T  I  S  R  D  K  S  Q  S  I  L

TATCTTCAAATGAACACCCTGAGAGCTGAGGACAGTGCCACTTATTACTGTACAAGAGAT
 Y  L  Q  M  N  T  L  R  A  E  D  S  A  T  Y  Y  C  T  R  D

AGGGGCTACGGTTCTACTTTGACTACTGGGGCCAAGGCACCACTCTCACAGTCTCCTCA
 R  G  L  R  F  Y  F  D  Y  W  G  Q  G  T  T  L  T  V  S  S
```

B

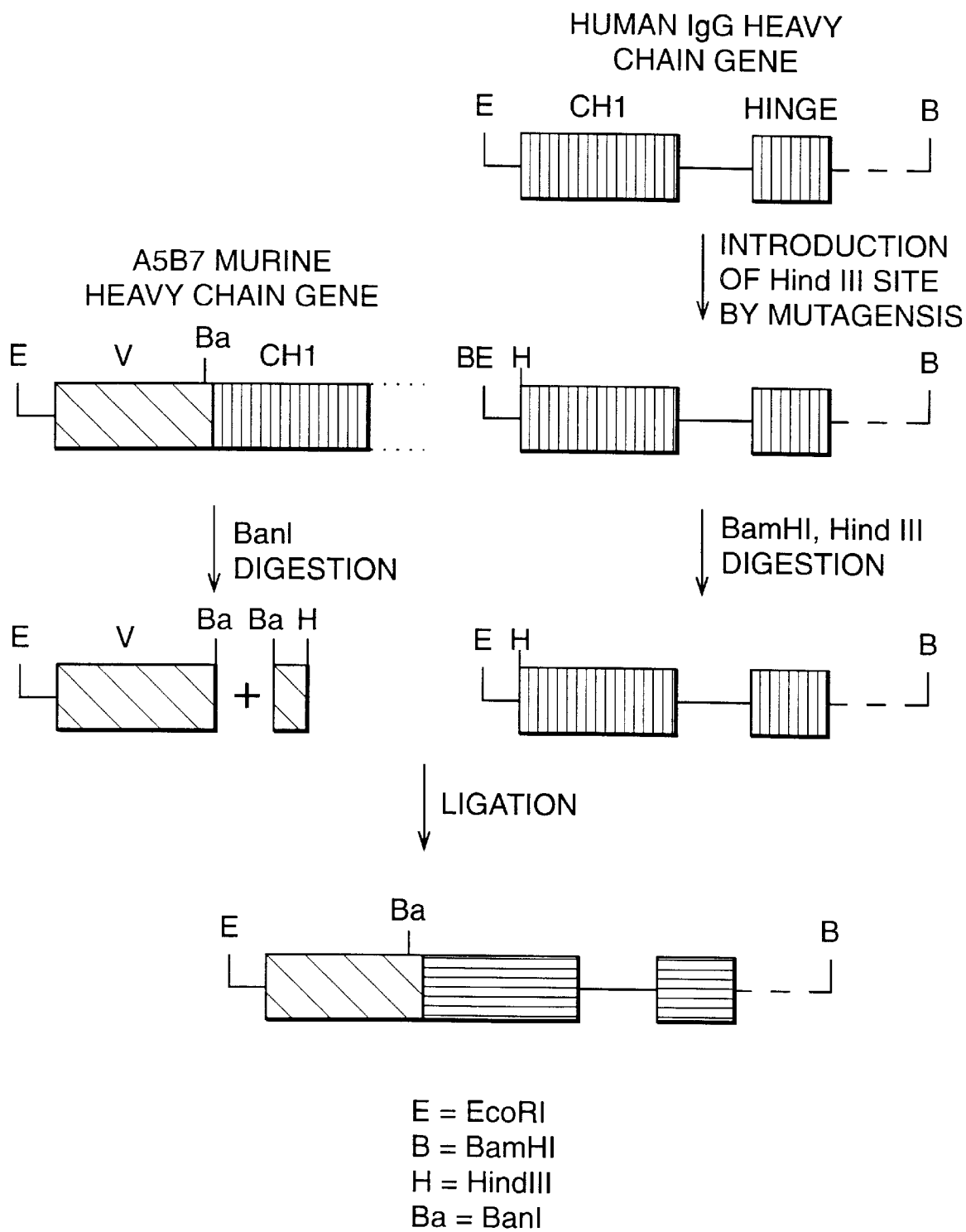

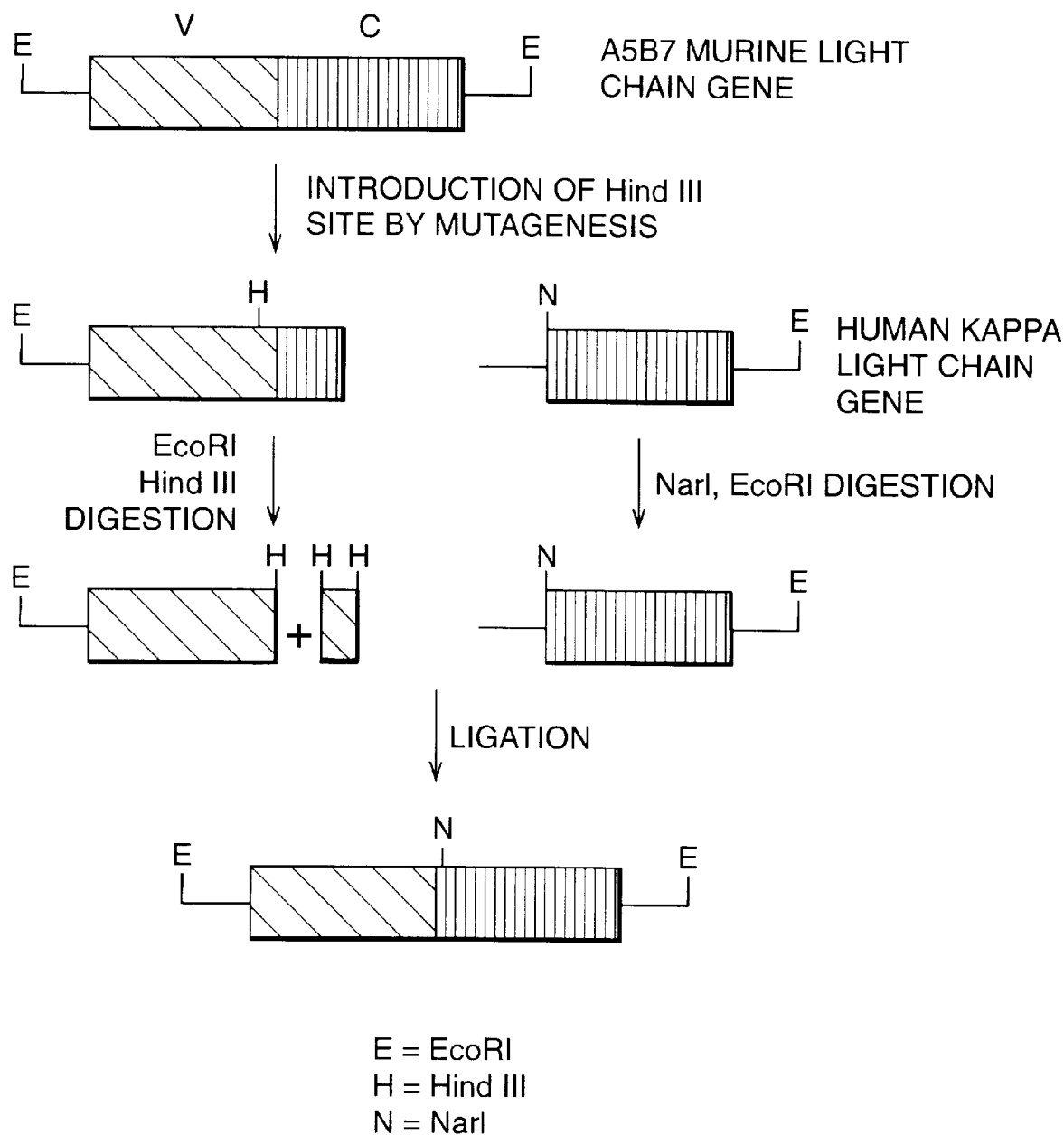

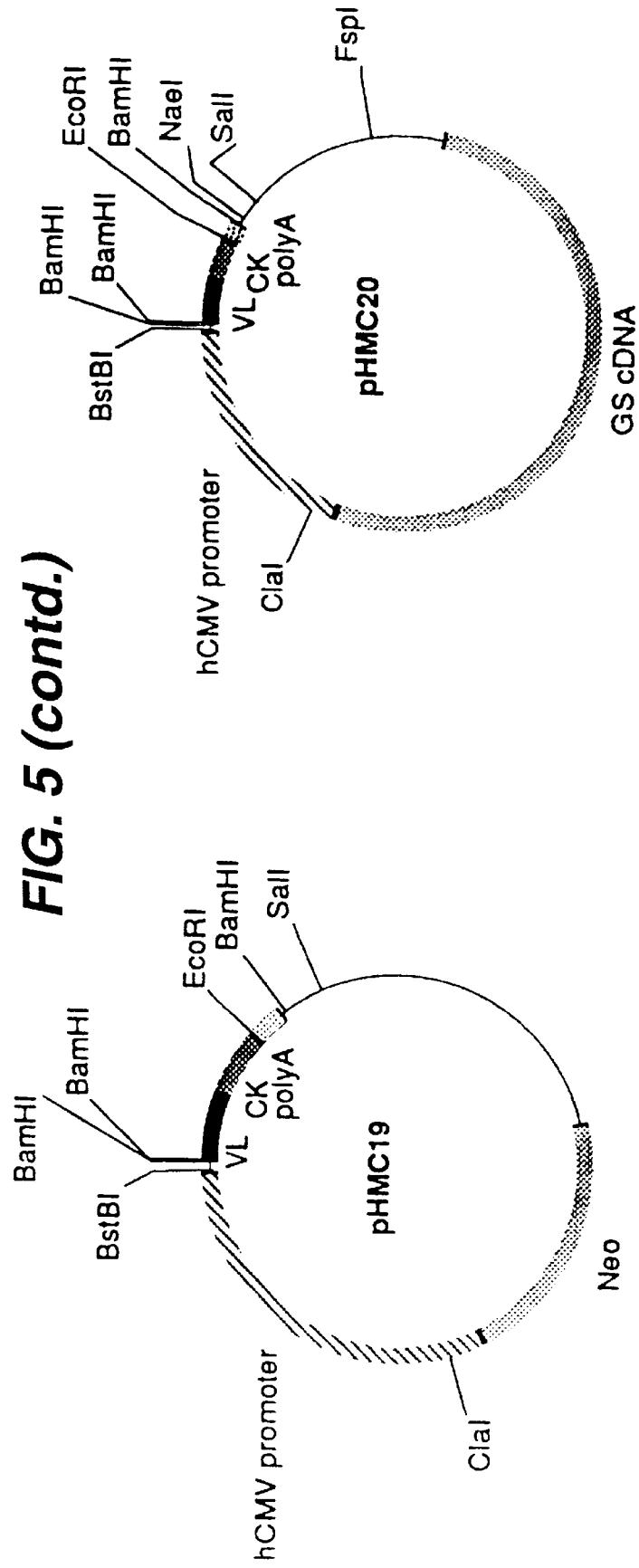
FIG. 5 (contd.)

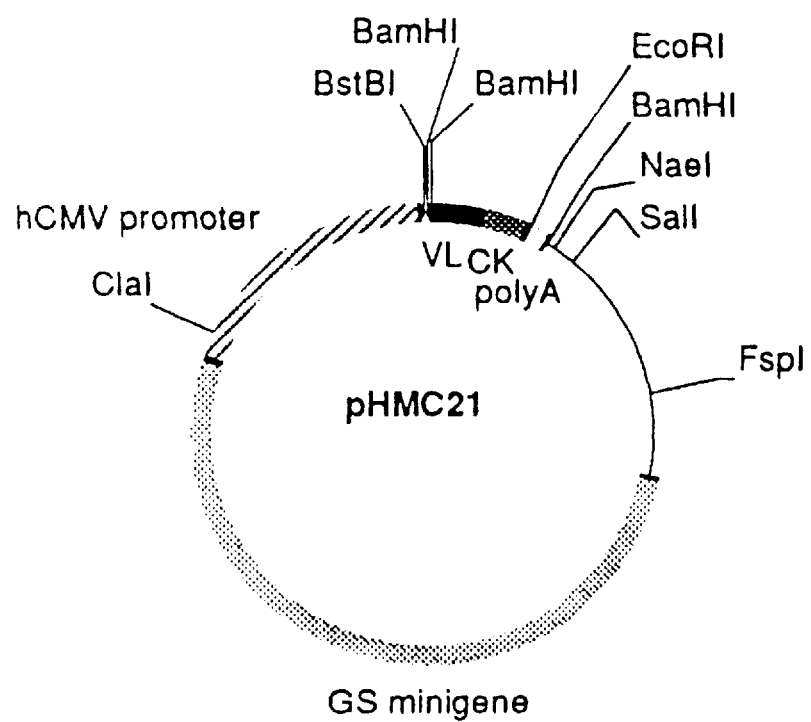
FIG. 5 (contd.)

GS vector for cL-cIgG1 expression in NS0 cells

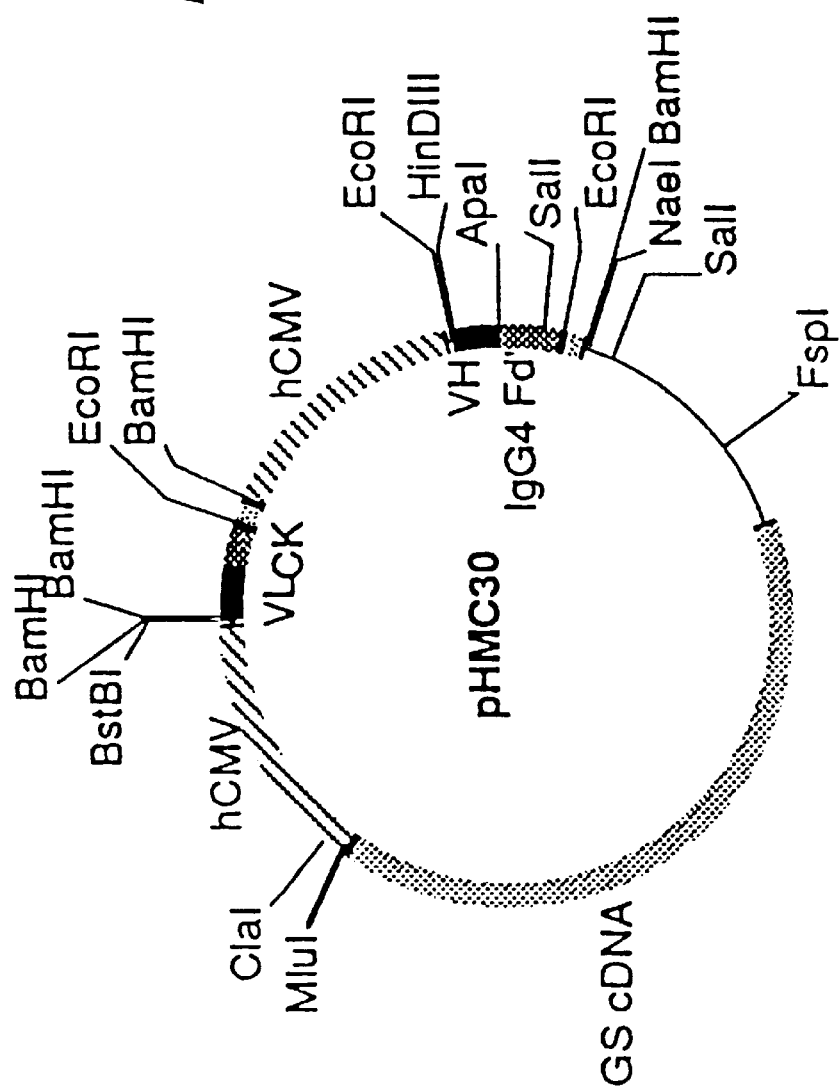
FIG. 6(contd)
GS vector for cL-cIgG4Fd' expression in NS0 cells

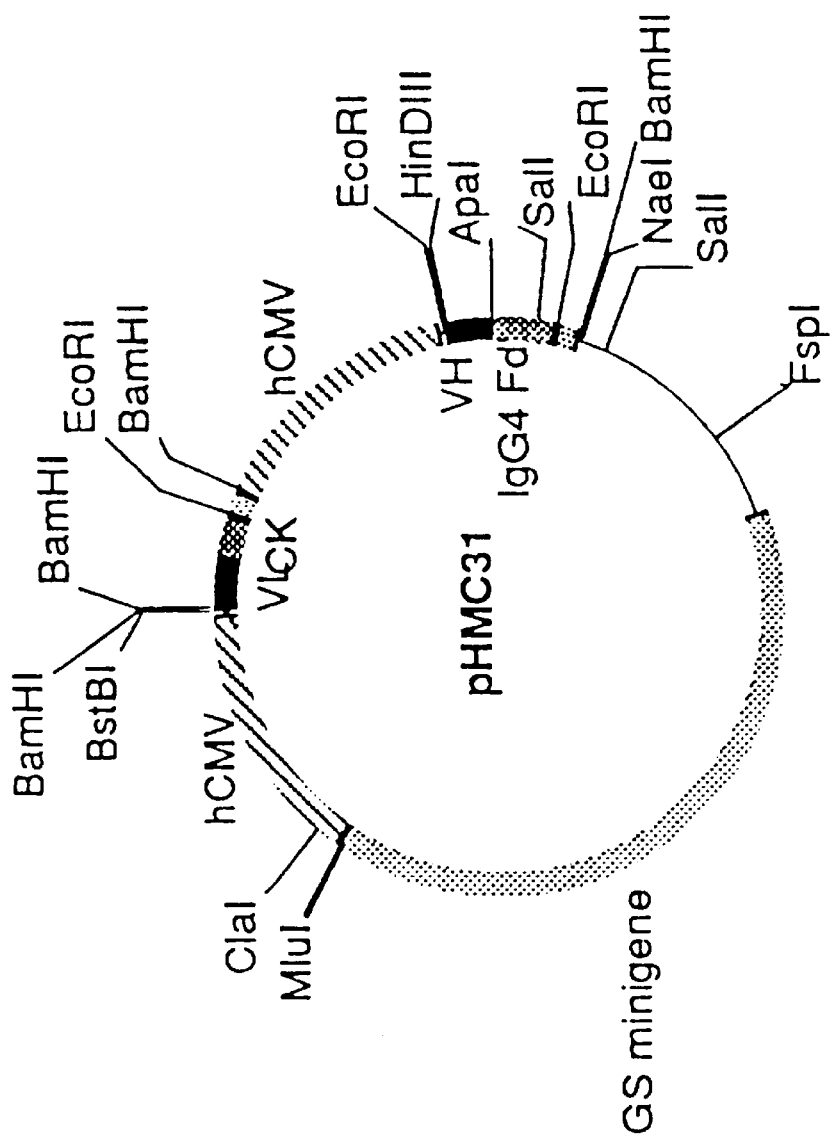
FIG. 6(contd) GS vector for cL-cIgG4Fd' expression in CHO cells

Purification and cross-linking of A5B7 cFab'

1. Molecular weight markers, non-reduced
2. A5B7 cDFM, non-reduced
3. A5B7 cFab', non-reduced
4. A5B7 cFab', reduced
5. A5B7 cDFM, reduced 10 - 20% acrylamide gradient gel, Coomassie blue stained

FIG. 8

```
                                      A5B7 LIGHT CHAIN GRAFT 1 (CONTD)
OLIGO L3    (87)
      K  S  L  I  Y  A  T  S  N  L  A  S  G  V  P  S  R  F  S  G  S  G  S  G
      AAAGTCTCTATCATCTATGCCACTAGTAACCTCGCCAGTGGTGTACCATCTAGATTCAGTGGTAGCGGTAGTG  +280
      ----+----+----+----+----+----+----+----+----+----+----+----+----+----+
      TTTCAGAGATAGTAGATACGGTGATCATTGGAGCGGTCACCACATGGTAGATCTAAGTCACCATCGCCATCAC
                                                                  XbaI           OLIGO L7  (90)

T  D  Y  T  F  T  I  S  S  L  Q  P  E  D  I  A  T  Y  Y  C  Q  H  W
      GTACTGATTATACTTTCACTATCAGTAGTCTCCAGCCAGAAGATATCGCCACTTACTATTGCCAGCATTG     +350
      ----+----+----+----+----+----+----+----+----+----+----+----+----+----+
      CATGACTAATATGAAAGTGATAGTCATCAGAGGTCGGTCTTCTATAGCGGTGAATGATAACGGTCGTAAC
                   OLIGO L4  (90)

S  S  K  P  P  T  F  G  Q  G  T  K  V  E  V  K  R  T
      GAGTAGTAAACCACCAACTTTCGGTCAGGGTACTAAAGTAGAAGTAAAACGTACGGGCCGG              +
      ----+----+----+----+----+----+----+----+----+----+----+----+
      CTCATCATTTGGTGGTTGAAAGCCAGTCCCATGATTTCATCTTCATTTTGCATGCCCGGCC
                                                   OLIGO L8  (21)
                                                   SplI
```

A5B7 LIGHT CHAIN GRAFT 2

```
                              M  S  V  P  T  Q  V  L  G  L  L  L  W  L  T  D
OLIGO L1 (21)
GGACTGTTCGAAGCCGCCACCATGTCTGTCCCCACCCAAGTCCTCGGACTCCTGCTGTGGCTTACAG    +70
------+---------+---------+---------+---------+---------+---------+
CCTGACAAGCTTCGGCGGTGGTACAGACAGGGGTGGGTTCAGGAGCCTGAGGACGACACCGAATGTC
       BstBI                                        OLIGO L5 (81)
            OLIGO L2 (81)
 A  R  C  Q  T  V  L  T  Q  S  P  S  S  L  S  V  S  V  G  D  R  V  T
ATGCCAGATGTCAGACTGTCACTCAGTCTCCATCCAGTCTGTAAGTGTCAGTGTGATAGGGTAAC    +140
------+---------+---------+---------+---------+---------+---------+
TACGGTCTACAGTCTGACAGTGAGTCAGAGGTAGGTCAGACATTCACATCCACTATCCCATTG
                                                OLIGO L6A (87)
 M  T  C  R  A  S  S  S  V  T  Y  I  H  W  Y  Q  Q  K  P  G  L  A  P
TATGACTTGTAGGGCCAGTAGTAGTGTAACTTATATCCATTGGTATCAGCAGAAACCAGGTCTCGCCCCA    +210
------+---------+---------+---------+---------+---------+---------+
ATACTGAACATCCCGGTCATCATCACATTGAATATAGGTAACCATAGTCGTCTTTGGTCCAGAGCGGGGT
```

A5B7 LIGHT CHAIN GRAFT 2 (CONTD)

```
         OLIGO L3A (87)
K  S  W  I  Y  A  T  S  N  L  A  S  G  V  P  S  R  F  S  G  S  G  S  G
AAAGTTGGATCTATGCCACTAGTAATCCGCCAGTGGTACCATCTAGATTCAGTGGTAGCGGTAGTG       +280
-----+---------+---------+---------+---------+---------+---------+
TTTCAACCTAGATACGGTGATCATTGGAGCGGTCACCATGGTAGATCTAAGTCACCATCGCCATCAC
                                                    XbaI    OLIGO L7A (90)

T  D  Y  T  L  T  I  S  S  L  Q  P  E  D  I  A  T  Y  Y  C  Q  H  W
GTACTGATTATACTCTCTCACTATCAGTAGTCTCCAGCCAGAAGATATCGCCACTTACTATTGCCAGCATTG     +350
-----+---------+---------+---------+---------+---------+---------+
CATGACTAATATGAGAGAGTGATAGTCATCAGAGGTCGGTTCTTCTATAGCGGTGAATGATAACGGTCGTAAC

OLIGO L4 (90)
S  S  K  P  P  T  F  G  Q  G  T  K  V  E  V  K  R  T
GAGTAGTAAACCACCAACTTTCGGTCAGGGTACTAAAGTAGAAGTAAAACGTACGGGCCGG          +
-----+---------+---------+---------+---------+---------+
CTCATCATTTGGTGGTTGAAAGCCAGTCCCATGATTTCATCTTCATTTTGCATGCCCGGCC
                                              OLIGO L8 (21)
                                              SplI
```

A5B7 HEAVY CHAIN GRAFT 1

```
OLIGO (I-1) H1 (21)
                                  M   E   W   S   W   V   F   F   L   F   F   L   S   V   T   T   G   V
              GCGCGCAAGCTTGCCGCCACCATGGAATGGAGCTGGGTCTTTCTCTTCCTGTCAGTAACTACAGAGAG   +70
              -----+---------+---------+---------+---------+---------+---------+
              CGCGCGTTCGAACGGCGGTGGTACCTTACCCTCGACCCAGAAAGAGAAGGACAGTCATTGATGTCCTC
              Hind III                         OLIGO H5 (90)

H   S   E   V   Q   L   L   E   S   G   G   G   L   V   Q   P   G   G   S   L   R   L   S
              TCCATTCTGAGGTGCAGCTGCTGGAGTCTGGAGGAGGCTTGGTGCAGCCTGGAGGATCTCTGAGACTGTC   +140
              -----+---------+---------+---------+---------+---------+---------+
              AGGTAAGACTCCACGTCGACGACCTCAGACCTCCTCCGAACCACGTCGGACCTCCTAGAGACTCTGACAG
                                                OLIGO H2 (96)

C   A   T   S   G   F   T   F   T   D   Y   Y   M   N   W   V   R   Q   A   P   G   K   G
              TTGTGCAACATCTGGATTCACCTTCACAGACTACTACATGAATTGGGTGAGACAGGCACCTGGAAAGGGA   +210
              -----+---------+---------+---------+---------+---------+---------+
              AACACGTTGTAGACCTAAGTGGAAGTGTCTGATGATGTACTTAACCCACTCTGTCCGTGGACCTTTCCCT
                                            OLIGO H6 (96)
```

A5B7 HEAVY CHAIN GRAFT 1 (CONTD)                           OLIGO H3 (96)

L   E   W   L   G   F   I   G   N   K   A   N   G   Y   T   E   Y   S   A   S   V   K   G
     CTCGAGTGGCTGGGCTTCATCGGAAATAAGGCAAATGGATACACAGAGTACTCTGCATCTGTGAAGG    +280
     ----+----+----+----+----+----+----+----+----+----+----+----+----+
     GAGCTCACCGACCCGAAGTAGCCTTTATTCCGTTTACCTATGTGTCTCATGAGACGTAGACACTTCC
     XhoI

R   F   T   I   S   R   D   K   S   K   S   T   L   Y   L   Q   M   N   G   L   Q   A   E
     GAAGATTCACAATTCCAGAGACAAGAGCAAGTCCACACTGTACCTGCAGATGAATGGACTGCAGGCAGA    +350
     ----+----+----+----+----+----+----+----+----+----+----+----+----+
     CTTCTAAGTGTTAAGGTCTCTGTTCTCGTTCAGGTGTGACATGGACGTCTACTTACCTGACGTCCGTCT
                                                        OLIGO H7 (96)

V   S   A   I   Y   Y   C   T   R   D   R   G   L   R   F   Y   F   D   Y   W   G   Q   G
     GGTGTCTGCAATTTACTACTGTACAAGAGACAGAGGACTGAGATTCTACTTCGACTACTGGGGACAGGGA    +420
     ----+----+----+----+----+----+----+----+----+----+----+----+----+
     CCACAGACGTTAAATGATGACATGTTCTCTGTCTCCTGACTCTAAGATGAAGCTGATGACCCCTGTCCCT

OLIGO H4 (95)
     T   L   V   T   V   S   S   A   S   T   K   G   P
     ACACTGGTGACAGTGTCTTCTGCCTCCACAAGGGCCCCGGCGC
     ----+----+----+----+----+----+----+----
     TGTGACCACTGTCACAGAAGACGGAGTTGCTTCCCGGGGCGCG
                              OLIGO I-1 H8 ApaI

A5B7 HEAVY CHAIN GRAFT 2

```
OLIGO (L-1) H1 (21)
                    M  E  W  S  W  V  F  L  F  F  L  S  V  T  T  G  V
         GCGCGCAAGCTTGCCGCCACCATGGAATGGAGCTGGGTCTTCTTCCTGTCAGTAACTACAGGAG
         ----+----+----+----+----+----+----+----+----+----+----+----+--  +70
         CGCGCGTTCGAACGGCGGTGGTACCTTACCTCGACCCAGAAGAAGGACAGTCATTGATGTCCTC
         Hind III                        OLIGO H5 (90)
                                                                 OLIGO H2 (96)
          H  S  E  V  Q  L  L  E  S  G  G  G  L  V  Q  P  G  G  S  L  R  L  S
         TCCATTCTGAGGTGCAGCTGCTGGAGTCTGGAGGAGGCTTGGTGCAGCCTGGAGGATCTCTGAGACTGTC
         ----+----+----+----+----+----+----+----+----+----+----+----+-- +140
         AGGTAAGACTCCACGTCGACGACCTCAGACCTCCTCCGAACCACGTCGGACCTCCTAGAGACTCTGACAG C  A  T  S  G  F  T  F  T  D  Y  Y  M  N  W  V  R  Q  A  P  G  K  G
         TTGTGCAACATCTGGATTCACCTTCACAGACTACTACATGAATTGGGTGAGACAGGCACCTGGAAAGGGA
         ----+----+----+----+----+----+----+----+----+----+----+----+-- +210
         AACACGTTGTAGACCTAAGTGGAAGTGTCTGATGATGTACTTAACCCACTCTGTCCGTGGACCTTTCCCT
                                          OLIGO H6 (96)
```

A5B7 HEAVY CHAIN GRAFT 2 (CONTD)         OLIGO H3 (96)

```
  L   E   W   L   G   F   I   G   N   K   A   N   G   Y   T   E   Y   S   A   S   V   K   G
  CTCGAGTGGCTGGGCTTCATCGGAAATAAGGCAAATGGATACACAACAGAGTACTCTGCATCTGTGAAGG   +280
  -------+---------+---------+---------+---------+---------+---------+
  GAGCTCACCGACCCGAAGTAGCCTTTATTCCGTTTACCTATGTGTTGTCTCATGAGACGTAGACACTTCC
  XhoI
```

```
  R   F   T   I   S   R   D   K   S   K   S   T   L   Y   L   Q   M   N   T   L   Q   A   E
  GAAGATTCACAATTTCCAGAGACAAGAGCAAGTCCACACTGTACCTGCAGATGAATACACTGCAGGCAGA   +350
  -------+---------+---------+---------+---------+---------+---------+
  CTTCTAAGTGTTAAAGGTCTCTGTTCTCGTTCAGGTGTGACATGGACGTCTACTTATGTGACGTCCGTCT
                                          OLIGO H7 (96)
```

```
  D   S   A   I   Y   Y   C   T   R   D   R   G   L   R   F   Y   F   D   Y   W   G   Q   G
  GGACTCTGCAATTTACTACTGTACAAGAGACAGAGGACTGAGATTCTACTTCGACTACTGGGGACAGGGA   +420
  -------+---------+---------+---------+---------+---------+---------+
  CCTGAGACGTTAAATGATGACATGTTCTCTGTCTCCTGACTCTAAGATGAAGCTGATGACCCCTGTCCCT
            OLIGO H4 (95)
```

```
  T   L   V   T   V   S   S   A   S   T   K   G   P
  ACACTGGTGACAGTGTCTTCTGCCTCAACGAAGGGCCCGGCGC
  -------+---------+---------+---------+-----
  TGTGACCACTGTCACAGAAGACGGAGTTGCTTCCCGGGCCGCG
                    OLIGO L -1 H8 ApaI
```

FIG.11(contd)

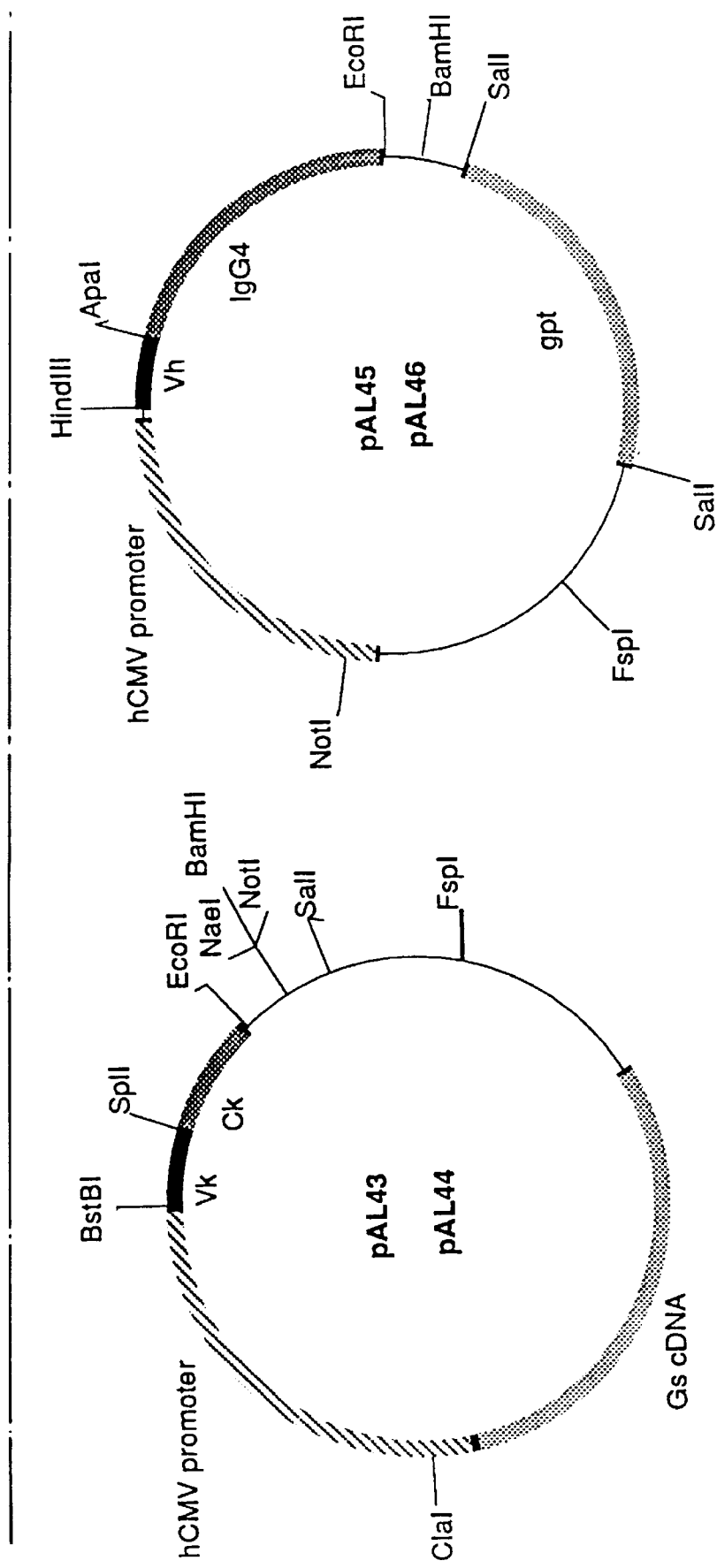
FIG. 12(contd)

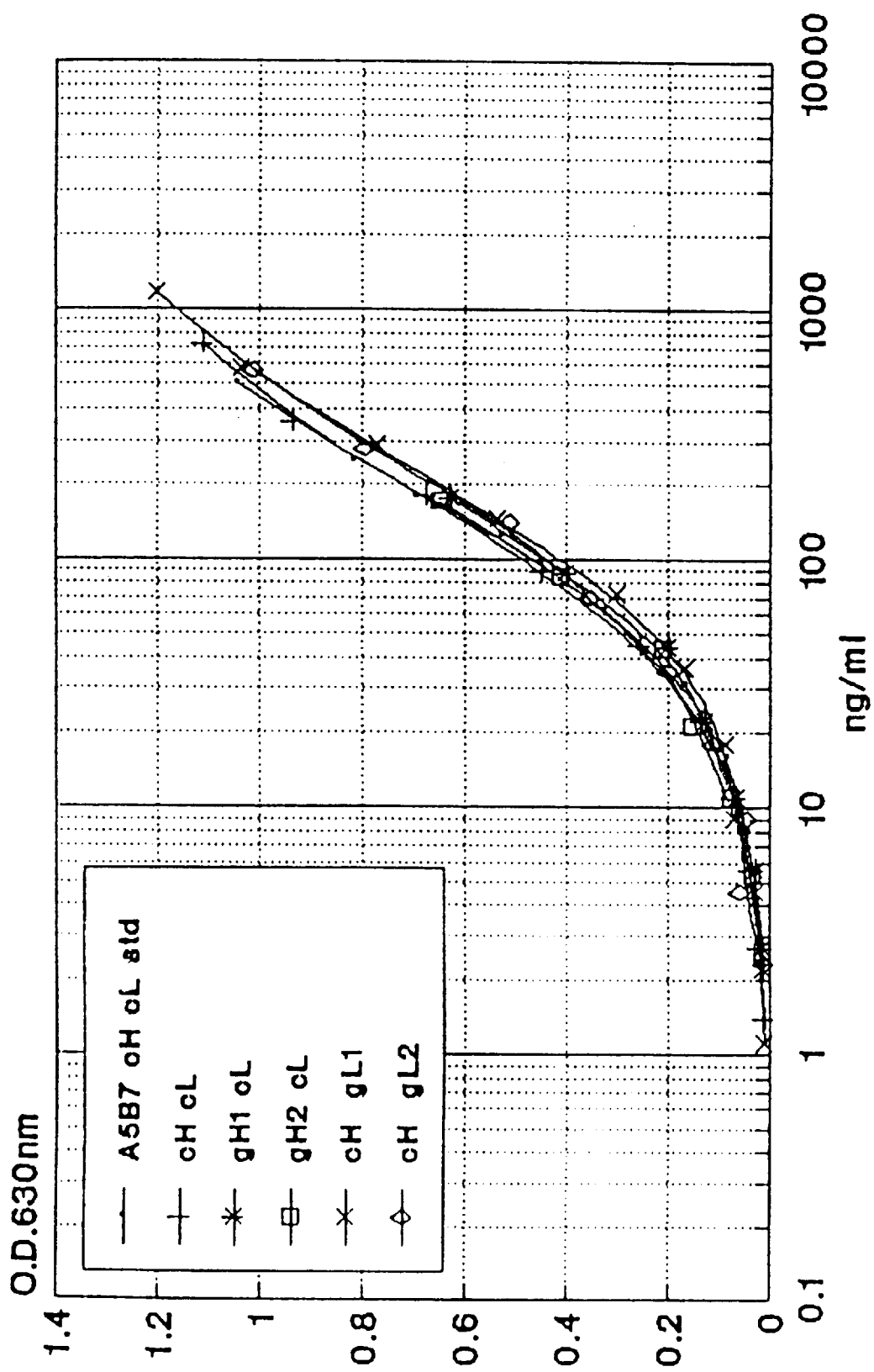

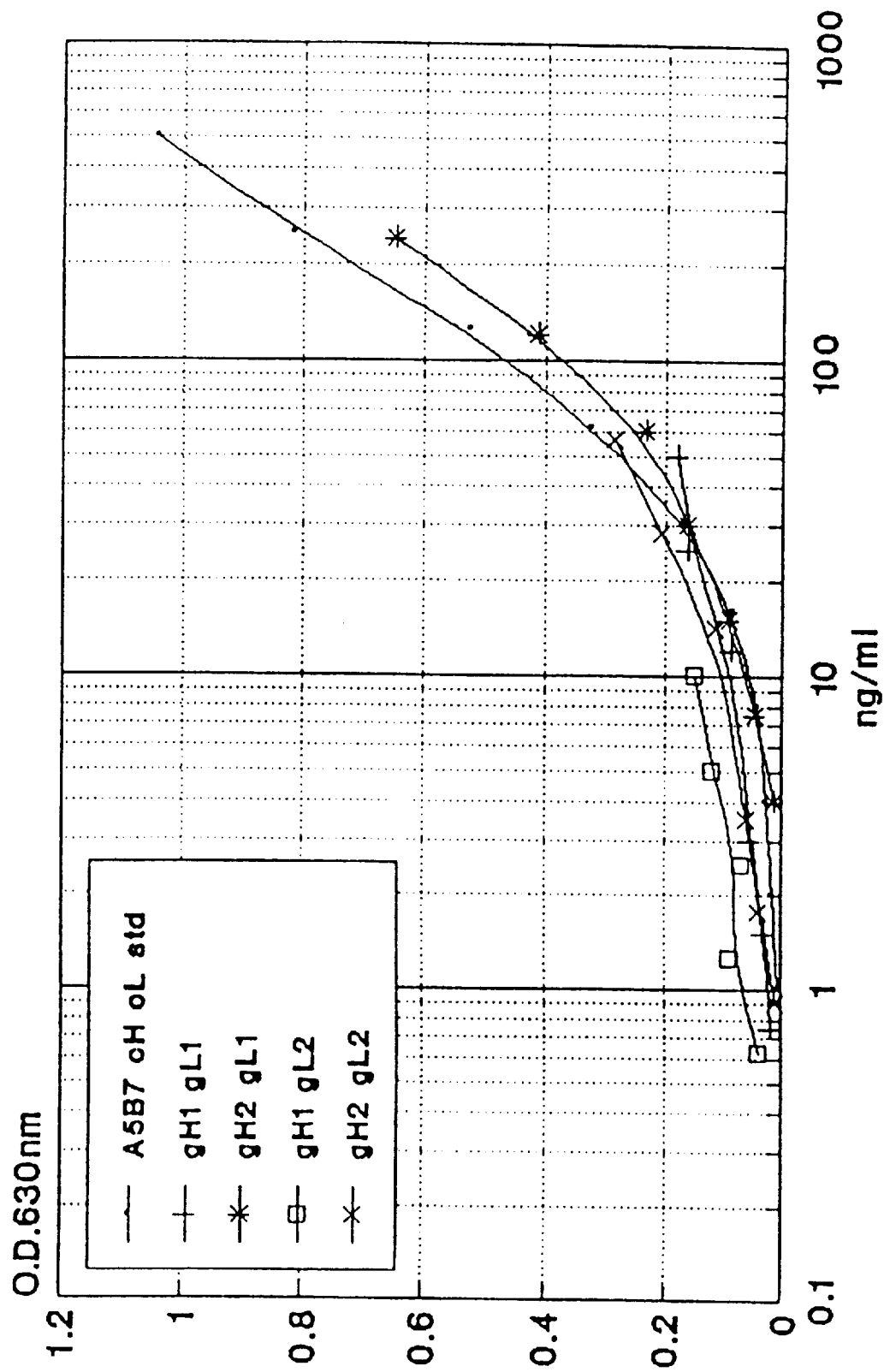

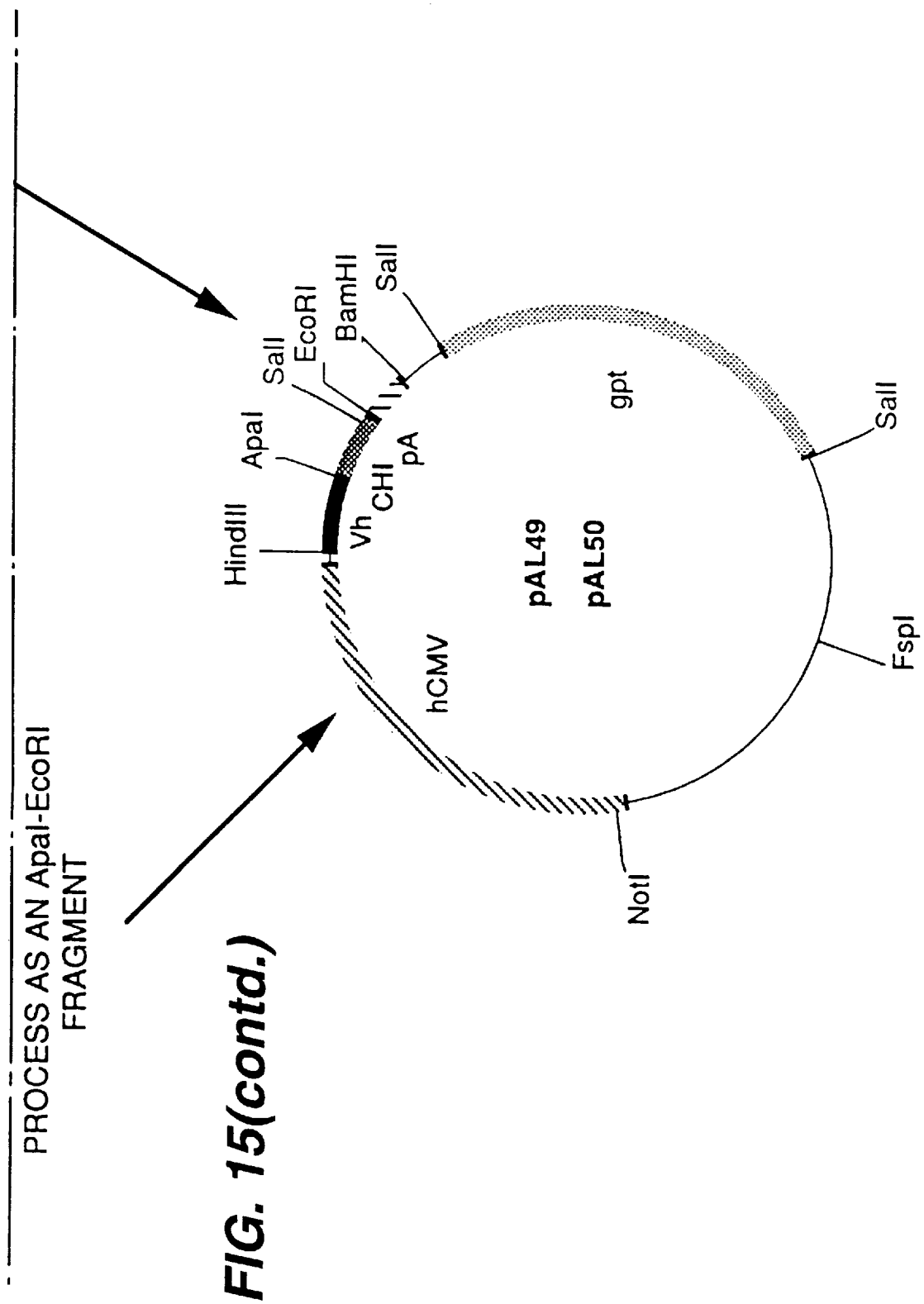
FIG. 15(contd.)

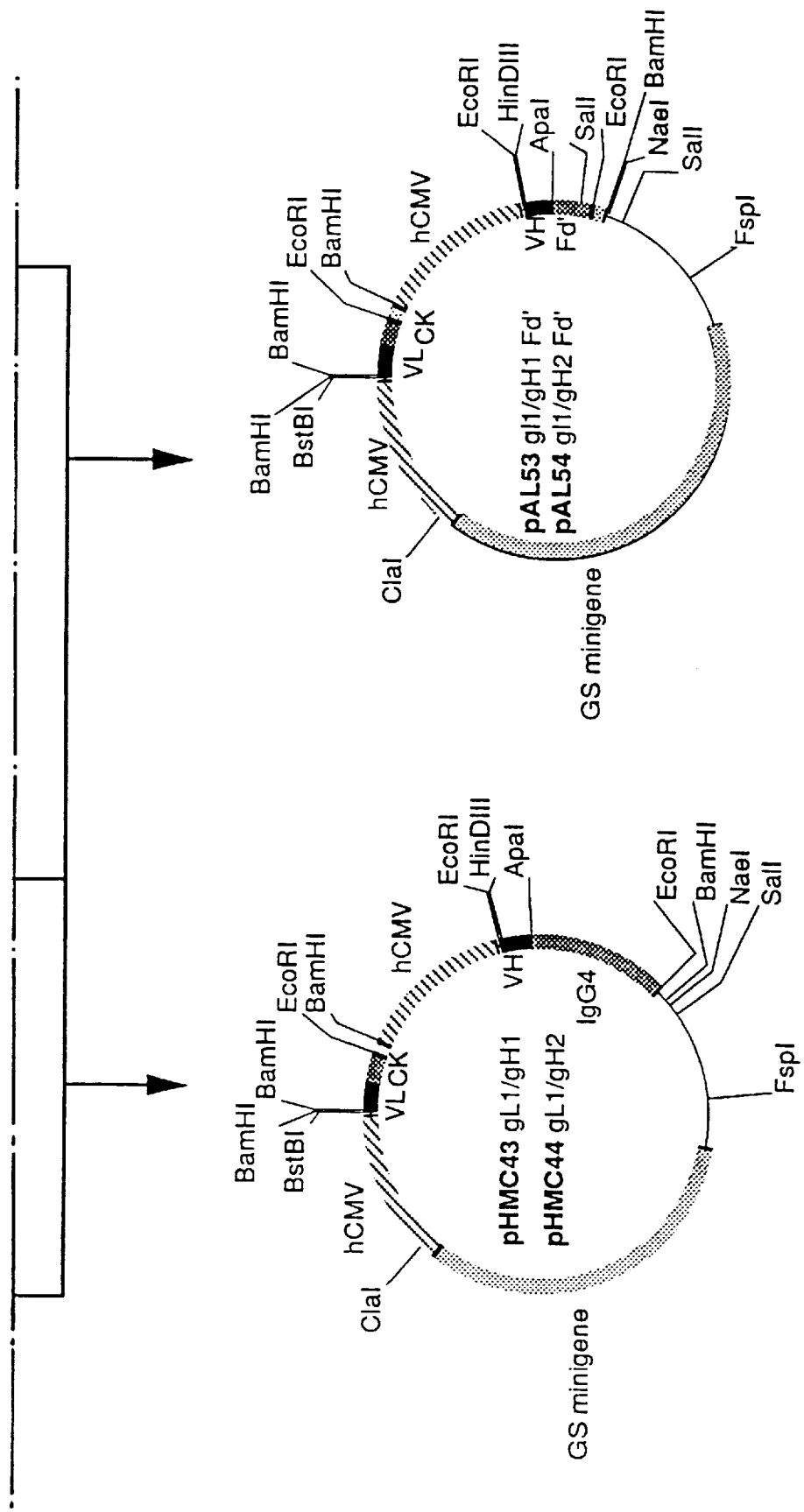
FIG. 16(contd.)

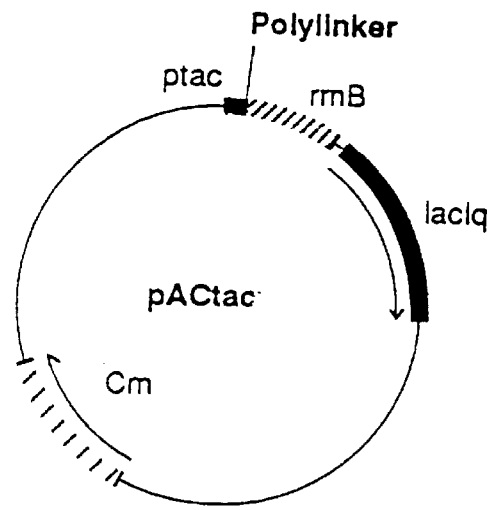
FIG. 17
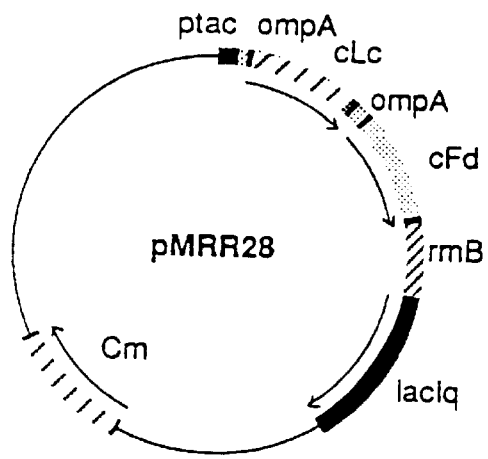
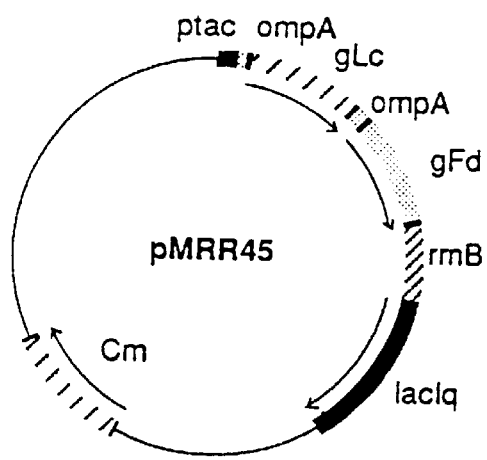

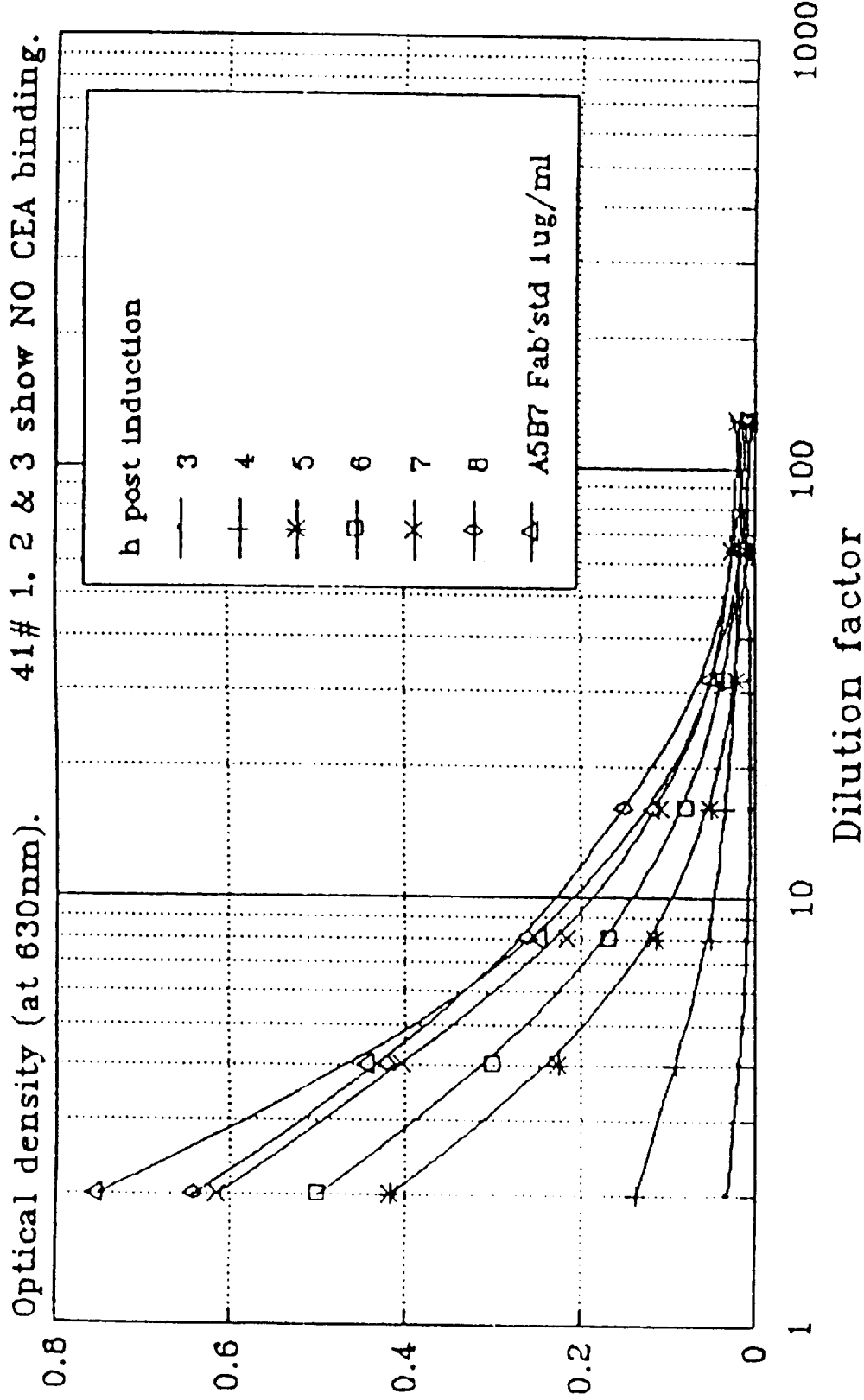

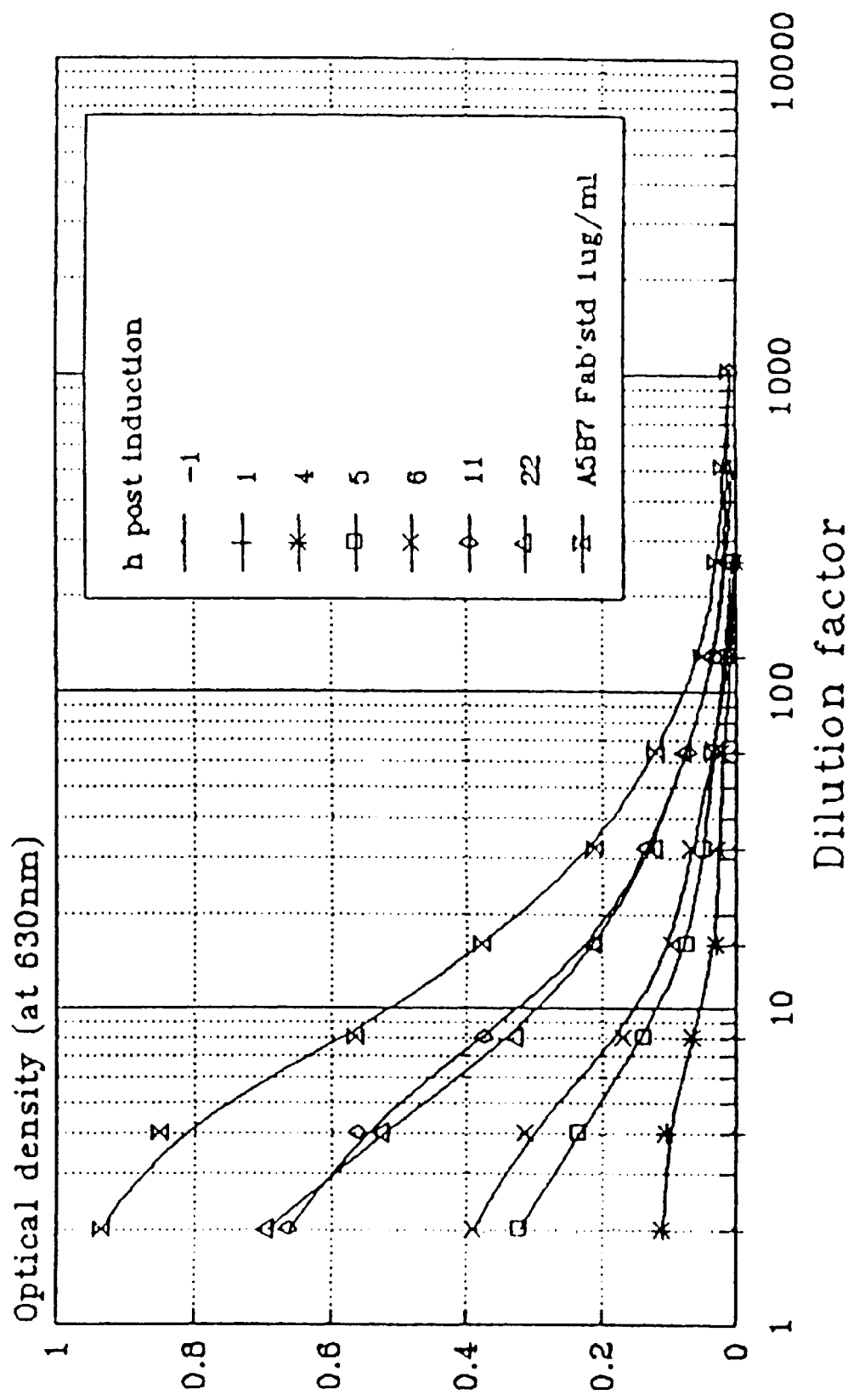
FIG. 19 CEA BINDING ASSAY ON E.COLI SUPERNATANTS CONTAINING A5B7 GRAFTED FAB'

CDR GRAFTED ANTI-CEA ANTIBODIES AND THEIR PRODUCTION

This is a continuation of application Ser. No. 08/154,389, filed Nov. 17, 1993, now abandoned, which is a continuation of Ser. No. 07/847,995, filed Apr. 21, 1992, now abandoned, which is a continuation of PCT/GB90/01108 filed Jul. 5, 1991.

FIELD OF THE INVENTION

The present invention relates to humanised antibody molecules (HAMs) having specificity for Carcinoembryonic Antigen (CEA) and to processes for their production using recombinant DNA technology.

The term "humanised antibody molecule" (HAM) is used to describe a molecule having an antigen binding site derived from an immunoglobulin from a non-human species, the remaining immunoglobulin-derived parts of the molecule being derived from a human immunoglobulin. The antigen binding site may comprise either complete variable domains fused onto human constant domains or only the complementarity determining regions (CDRs) grafted onto appropriate human framework regions in the variable domains. The abbreviation "MAb" is used to indicate a monoclonal antibody.

In the description, reference is made to publications by number, and these publications are listed in numerical order at the end of the description.

BACKGROUND OF THE INVENTION

Natural immunoglobulins have been known for many years, as have the various fragments thereof, such as the Fab, (Fab')$_2$ and Fc fragments, which can be derived by enzymatic cleavage. Natural immunoglobulins comprise a generally Y-shaped molecule having an antigen-binding site towards the outer end of each upper arm. The remainder of the structure, and particularly the stem of the Y, mediates the effector functions associated with immunoglobulins.

Natural immunoglobulins have been used in assay, diagnosis and, to a more limited extent, therapy. However, such uses, especially in therapy, have been hindered by the polyclonal nature of natural immunoglobulins. A significant step towards the realisation of the potential of immunoglobulins as therapeutic agents was the discovery of procedures for the production of monoclonal antibodies of defined specificity (1). However, most MAbs are produced by hybridomas which are fusions of rodent spleen cells with rodent myeloma cells. The resultant MAbs are therefore essentially rodent proteins. There are very few reports of the production of human MAbs.

Since most available MAbs are of rodent origin, they are naturally antigenic in humans and thus can give rise to an undesirable immune response termed the HAMA (Human Anti-Mouse Antibody) response. Therefore, the use of rodent MAbs as therapeutic agents in humans is inherently limited by the fact that the human subject will mount an immunological response to the MAb and will either remove it entirely or at least reduce its effectiveness.

Therefore proposals have been made for making non-human MAbs less antigenic in humans. Such techniques can be generically termed "humanisation" techniques. These techniques generally involve the use of recombinant DNA technology to manipulate DNA sequences encoding the polypeptide chains of the antibody molecule.

Early methods for humanising MAbs related to production of chimeric antibodies in which an antigen binding site comprising the complete variable domains of one antibody are fused to constant domains derived from a second antibody. Methods for carrying out such chimerisation procedures are described in EP0120694 (Celltech Limited), EP0125023 (Genentech Inc.), EP-A-0171496 (Res. Dev. Corp. Japan), EP-A-0173494 (Stanford University), and EP-A-0194276 (Celltech Limited). The Celltech EP 0194276 application discloses a process for preparing an antibody molecule having the variable domains from a mouse MAb and the constant domains from a human immunoglobulin. It also describes the production of an antibody molecule comprising the variable domains of a mouse MAb, the CH1 and CL domains of a human immunoglobulin, and a non-immunoglobulin-derived protein in place of the Fc portion of the human immunoglobulin.

Subsequently a number of further patent applications have been published relating to chimeric antibodies, including tumour specific chimeric antibodies (e.g. WO 87/02671, Int. Gen. Eng. Inc.; EP 0256654, Centocor; EP 0266663, Int. Gen. Eng. Inc. & Oncogen; WO 89/00999, Int. Gen. Eng. Inc. and EP 0332424, Hybritech Inc.). The Genentech (EP0125023) and Hybritech (EP0332424) patent applications relate to anti-carcinoembryonic antigen (anti-CEA) chimeric antibodies.

Such humanised chimeric antibodies, however, still contain a significant proportion of non-human amino acid sequence, i.e. the complete variable domains. Thus such humanised antibodies may elicit some HAMA response, particularly if administered over a prolonged period [Begent et al (ref. 2)].

In an alternative approach, described in EP-A-02394000 (Winter), the complementarity determining regions (CDRs) of a mouse MAb have been grafted onto the framework regions of the variable domains of a human immunoglobulin by site directed mutagenesis using long oligonucleotides. Such CDR-grafted humanised antibodies are less likely to give rise to a HAMA response than humanised chimeric antibodies in view of the lower proportion of non-human amino acid sequence which they contain. There are 3 CDRs (CDR1, CDR2 and CDR3) in each of the heavy and light chain variable domains.

The earliest work on CDR-grafted humanised MAbs was carried out on MAbs recognising synthetic antigens, such as the NP or NIP antigens. However, recently examples in which a mouse MAb recognising lysozyme and a rat MAb recognising an antigen on human T cells respectively were humanised have been described by Verhoeyen et al (3) and Riechmann et al (4). The preparation of the CDR-grafted antibody to the antigen on human T cells is also described in WO 89/07452 (Medical Research Council). More recently Queen et al (5) have described the preparation of a humanised CDR-grafted antibody that binds to the interleukin 2 receptor.

It has been widely suggested that immunoglobulins, and in particular MAbs, could potentially be very useful in the diagnosis and treatment of cancer (6, 7). There has therefore been much activity in trying to produce immunoglobulins or MAbs directed against tumour-specific antigens. So far, over one hundred MAbs directed against a variety of human carcinomas have been used in various aspects of tumour diagnosis or treatment (8).

There have been a number of papers published concerning the production of chimeric monoclonal antibodies recognising cell surface antigens. For instance, Sahagan et al (9) disclose a genetically engineered murine/human chimeric antibody which retains specificity for a tumour-associated antigen. Also Nishimura et al (10) disclose a recombinant murine/human chimeric monoclonal antibody specific for common acute lymphocytic leukemia antigen.

We have now prepared humanised antibodies to carcinoembryonic antigen derived from the anti-CEA mouse MAb A5B7 (11).

Our copending International Patent Application PCT/GB 90/02017 relates to the CDR-grafting of antibodies in general and describes, among other things, that antibodies having specificity for cancer markers such as CEA, e.g. the A5B7 monoclonal antibody, have been successfully CDR-grafted according to the procedure described therein.

SUMMARY OF THE INVENTION

According to the present invention, there is provided a humanised antibody molecule (HAM) having specificity for carcinoembryonic antigen (CEA) and having an antigen binding site wherein at least one of the complementarity determining regions (CDRs) of the variable domain is derived from the mouse monoclonal antibody A5B7 (A5B7 MAb) and the remaining immunoglobulin-derived parts of the HAM are derived from a human immunoglobulin.

GENERAL DESCRIPTION OF THE INVENTION

The HAM may comprise a chimeric humanised antibody or a CDR-grafted humanised antibody. When the HAM comprises a CDR-grafted humanised antibody, the heavy and/or light chain variable domains may comprise only one or two A5B7 derived CDRs; though preferably all three heavy and light chain CDRs are derived from A5B7.

The A5B7 MAb is a mouse MAb of the type IgG1-Kappa raised against purified CEA which had been denatured by heating to 85° C. for 35 minutes. The A5B7 MAb has been extensively studied at Charing Cross Hospital, London, UK (11). Immunohistochemical studies have demonstrated that the A5B7 MAb reacts with CEA producing tumours. Its distribution is within malignant glands in the cell cytoplasm, at the cell surface and in necrotic debris. However, it shows no significant cross-reactivity with a wide spectrum of normal human tissues. The molecular cloning and sequencing of the A5B7 heavy and light chain cDNAs is described hereinafter and the $V_L$ and $V_H$ cDNA and predicted amino acid sequences are given in FIG. 1.

Surprisingly it has been found that humanising the A5B7 MAb, in particular by CDR-grafting, does not substantially adversely affect its binding activity, and this produces a HAM which is extremely useful in both therapy and diagnosis of certain carcinomas.

Preferably, the HAM of the present invention is produced by recombinant DNA technology.

The HAM of the present invention may comprise: a complete antibody molecule, having full length heavy and light chains; a fragment thereof, such as the Fab, Fab', (Fab')$_2$ or FV fragment; a single chain antibody fragment, e.g. a single chain FV; a light chain or heavy chain monomer or dimer; including fragments or analogues of any of these or any other molecule with the same specificity as the A5B7 antibody.

The HAM of the present invention may have attached to it an effector or reporter molecule. For instance, the HAM may have a macrocycle for chelating a heavy metal atom, or a toxin such as ricin, attached to it by a covalent bridging structure. Alternatively, the procedures of recombinant DNA technology may be used to produce a HAM in which the Fc fragment, CH3 or CH4 domain of a complete antibody molecule has been replaced by or has attached thereto by peptide linkage a functional non-immunoglobulin protein, such as an enzyme or toxin molecule.

The remaining non-A5B7, immunoglobulin derived parts of the HAM may be derived from any suitable human immunoglobulin. For instance, when the HAM is a CDR-grafted HAM, appropriate variable region framework sequences may be used having regard to class/type of the A5B7 donor antibody from which the antigen binding regions are derived. Preferably, the type of human framework used is of the same/similar class/type as the donor antibody (A5B7 is IgG1 Kappa). Advantageously, the framework is chosen to maximise/optimise homology with the donor antibody sequence particularly at positions spacially close or adjacent to the CDRs. Examples of human frameworks which may be used to construct CDR-grafted HAMs are LAY, POM, TUR, TEI, KOL, NEWM, REI and EU; for instance KOL and NEWM for the heavy chain and REI for the light chain and EU for both the heavy chain and the light chain. Preferably the LAY framework is used as the human framework for both heavy and light chain variable domains, in view of its high level of homology with A5B7.

Also human constant domains of the HAM may be selected having regard to the proposed function of the antibody, in particular the effector functions which may be required. For example, the constant domains may be human IgA, IgE, IgG or IgM domains. In particular, IgG human constant domains may be used especially of the IgG1 and IgG3 isotypes, when the HAM is intended for therapeutic purposes and antibody effector functions are required. Alternatively, IgG2 and IgG4 isotypes may be used when the HAM is intended for purposes for which antibody effector functions are not required e.g. for imaging, diagnostic or cytotoxic targeting purposes.

However, the remainder of the HAM need not comprise only protein sequences from human immunoglobulins. For instance, a gene may be constructed in which a DNA sequence encoding part of a human immunoglobulin chain is fused to a DNA sequence encoding the amino acid sequence of a polypeptide effector or reporter molecule.

According to a second aspect of the present invention, there is provided a process for producing the HAM of the first aspect of the invention, which process comprises:

(a) producing in an expression vector an operon having a DNA sequence which encodes an antibody heavy or light chain comprising a variable domain wherein at least one of the CDRs of the variable domain is derived from the A5B7 MAb and the remaining immunoglobulin-derived parts of the antibody chain are derived from a human immunoglobulin;

(b) producing in an expression vector an operon having a DNA sequence which encodes a complementary antibody light or heavy chain comprising a variable domain wherein at least one of the CDRs of the variable domain is derived from the A5B7 MAb and the remaining immunoglobulin-derived parts of the antibody chain are derived from a human immunoglobulin;

(c) transfecting a host cell with the or each vector; and (d) culturing the transfected cell line to produce the HAM.

The cell line may be transfected with two vectors, the first vector containing an operon encoding a light chain-derived polypeptide and the second vector containing an operon encoding a heavy chain-derived polypeptide. Preferably, the vectors are identical except in so far as the coding sequences and selectable markers are concerned so as to ensure as far as possible that each polypeptide chain is equally expressed.

Alternatively, a single vector may be used, the vector including the sequences encoding both light chain- and heavy chain-derived polypeptides.

Thus in further aspects the invention also includes DNA sequences coding for the heavy and light chains, cloning and expression vectors containing the DNA sequences, host cells transformed with the DNA sequences and processes for producing the heavy and/or light chains and antibody molecules comprising expressing the DNA sequences in the transformed host cells.

The general methods by which the vectors may be constructed, transfection methods and culture methods are well known per se. Such methods are shown, for instance, in references 12 and 13.

The DNA sequences which encode the A5B7 amino acid sequence may be obtained by methods well known in the art. For example, the A5B7 coding sequences may be obtained by genomic cloning, or cDNA cloning from the A5B7 hybridoma cell line. Positive clones may be screened using appropriate probes for the heavy and light chain genes in question. Also PCR cloning may be used.

DNA coding for human immunoglobulin sequences may be obtained in any appropriate way. For example, DNA sequences coding for preferred human acceptor frameworks such as LAY, POM, KOL, REI, EU, TUR, TEI and NEWM, are widely available to workers in the art.

The standard techniques of molecular biology may be used to prepare DNA sequences coding for the CDR-grafted products. Desired DNA sequences may be synthesised completely or in part using oligonucleotide synthesis techniques. Site-directed mutagenesis and polymerase chain reaction (PCR) techniques may be used as appropriate. For example, oligonucleotide directed synthesis as described by Jones et al (14) may be used. Also oligonucleotide directed mutagenesis of a pre-existing variable region as, for example, described by Verhoeyen et al (3) or Riechmann et al (4) may be used. Also enzymatic filling in of gapped oligonucleotides using $T_4$ DNA polymerase as, for example, described by Queen et al (5) may be used.

Any suitable host cell/vector system may be used for expression of the DNA sequences coding for the chimeric CDR-grafted heavy and light chains. Bacterial e.g. *E. coli*, and other microbial systems may be used, in particular for expression of antibody fragments, e.g. FV, Fab and Fab' fragments, and single chain antibody fragments e.g. single chain FVs. Eucaryotic e.g. mammalian host cell expression systems may be used for production of larger CDR-grafted antibody products, including complete antibody molecules. Suitable mammalian host cells include CHO cells and myeloma or hybridoma cell lines.

The present invention also includes therapeutic and diagnostic compositions containing the HAM of the invention and uses of such compositions in therapy and diagnosis.

Such therapeutic and diagnostic compositions typically comprise a HAM according to the invention in combination with a pharmaceutically acceptable excipient diluent or carrier, e.g. for in vivo use. Therapeutic and diagnostic uses typically comprise administering an effective amount of a HAM according to the invention to a human subject.

In the HAM of the first aspect of the invention and the process of the second aspect of the invention the heavy and light chain variable domains of the HAM may comprise either the entire variable domains of the A5B7 MAb or may comprise framework regions of a human variable domain having grafted thereon one, some or all of the CDRs of the A5B7 MAb. Thus the HAM may comprise a chimeric humanised antibody or a CDR-grafted humanised antibody.

When the HAM is a CDR-grafted humanised antibody, in addition to the CDRs, specific variable region framework residues may correspond to non-human, i.e. the A5B7 mouse, residues. Preferably the CDR-grafted humanised antibodies of the present invention include CDR-grafted humanised antibodies as defined in our co-pending patent application, International Patent Application PCT/GB 90/02017. The disclosure of PCT/GB 90/02017 is incorporated herein by reference.

Preferably the CDRs of the light chain correspond to the Kabat CDRs at CDR1 (positions 24–34) and CDR2 (positions 50–56) and to the structural loop residues positions 91–96) or Kabat CDR residues (positions 89–97) in CDR3. In addition the light chain may have mouse residues at one or more of positions 1, 2 and/or 3, 46, 47, 49, 60, 70, 84, 85 and 87 and preferably has mouse residues at at least positions 46 and 47.

In addition to the CDRs, the HAM heavy chain preferably has mouse residues at positions 23 and/or 24 and 71 and/or 73. Additionally, the heavy chain may have mouse residues at one, some or all of positions 48 and/or 49, 69, 76 and/or 78, 80, 88 and/or 91 and 6. Preferably also, the CDRs of the heavy chain correspond to the Kabat CDR at CDR2 (positions 50–65), the structural loop residues at CDR3 (positions 95–100) and a composite of both the Kabat and structural loop residues at CDR1 (positions 24–35); for example, when the human variable region framework used is KOL. Alternatively, the CDRs of the heavy chain may comprise mouse residues at positions 26 to 35 for CDR1, positions 50 to 65 for CDR2 and positions 94 to 100 for CDR3; for example, when the human variable region framework used in EU. In addition EU has a particularly idiosyncratic J region between residues 103 to 113 and it may be useful to include the murine amino acids, or a consensus human J region or a suitable combination of both at residues 103 to 108 inclusive.

In a particularly preferred embodiment LAY human variable region frameworks are used for both the CDR-grafted heavy and light chains, in which case the light chain preferably comprises mouse A5B7 residues at positions 1, 2, 3, 4, 46 and 71, and especially also at positions 21, 47 and 73, of the variable domain frameworks. Similarly, the heavy chain preferably comprises mouse A5B7 residues at positions 1, 24, 48, 49, 72, 73, 76 and 93, and especially also at positions 82b and 86, of the variable domain frameworks. Also when the LAY human variable domain frameworks are used, the variable domains preferably comprises A5B7 mouse CDRs at residues 24 to 34 (CDR1) 50 to 56 (CDR2) and 89 to 97 (CDR3) for the light chain and at residues 26 to 35 (CDR1), 50 to 65 (CDR3) and 95 to 102 (CDR3) for the heavy chain.

The residue designations given above and elsewhere in the present application are numbered according to the Kabat numbering (15).

BRIEF DESCRIPTION OF THE DRAWINGS

The present invention is now described, by way of illustration only, in the following examples which refer to the accompanying FIGS. 1–19, in which:

FIG. 1 shows the DNA sequences (SEQ ID NOS. 1 and 3) encoding the unprocessed variable regions of the A5B7 MAb obtained by sequencing cDNA clones together with the predicted amino acid sequence; (SEQ ID NOS. 2 and 4)

FIG. 2 is a schematic diagram of the construction by restriction and ligation of the chimeric heavy chain gene;

FIG. 3 is a schematic diagram of the construction by site-directed mutagenesis, restriction and ligation of the chimeric light chain gene;

Figure 8:
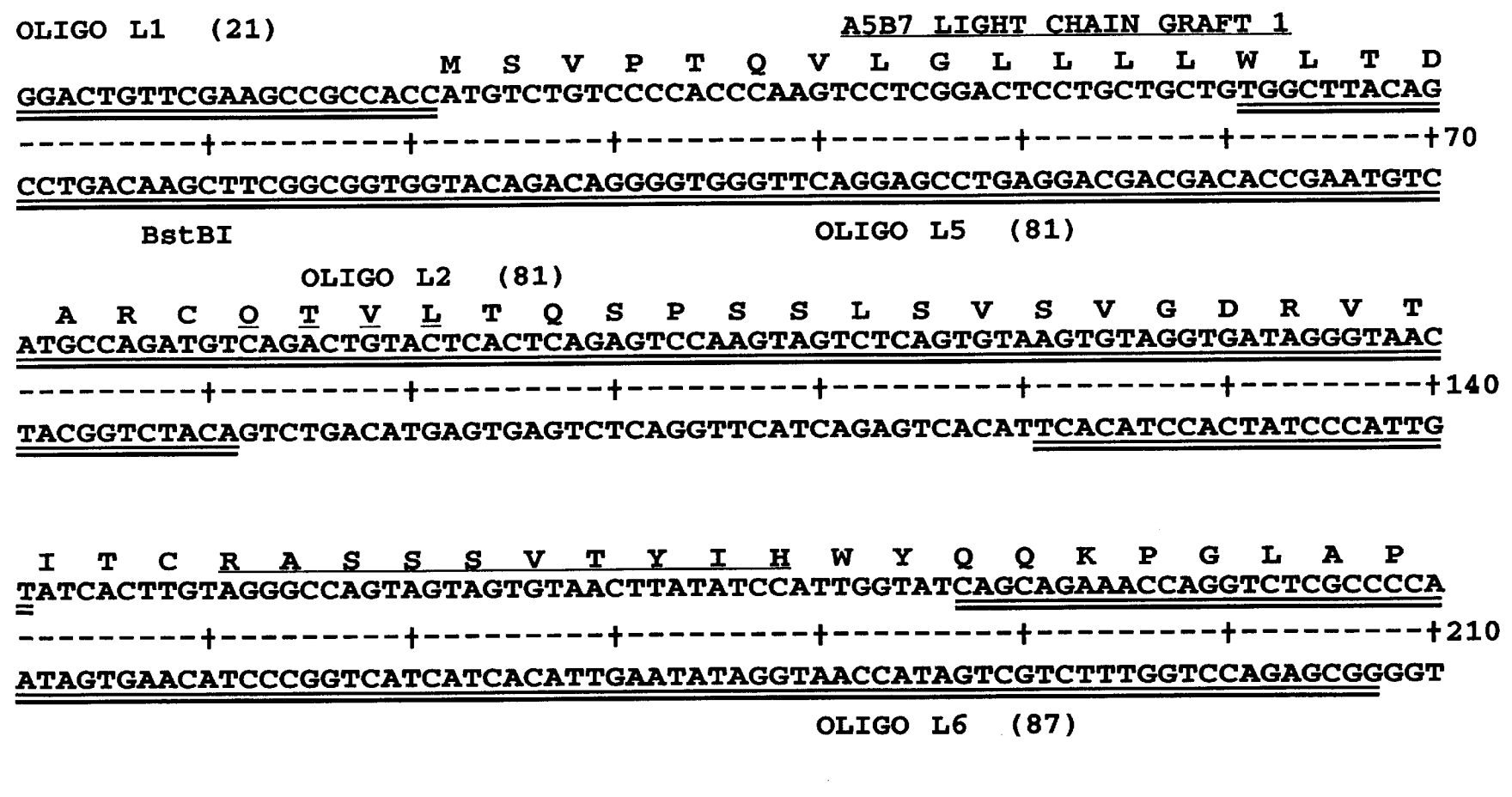

FIG. 8 shows the DNA and protein sequences (SEQ ID NOS. 5 and 6) for the A5B7 grafted light chain, gL-1 variable domain;

FIG. 9 shows similar sequences (SEQ ID NOS. 7 and 8) for the A5B7 grafted light chain gL-2, variable domain;

FIG. 10 shows similar sequences (SEQ ID NOS. 9 and 10) for the A5B7 grafted heavy chain gH1, variable domain;

FIG. 11 shows similar sequences (SEQ ID NOS. 11 and 12) for the A5B7 grafted heavy chain-gH2, variable domain.

FIG. 13 is graphs showing the results of direct CEA binding ELISAs on supernatants from transient expression of chimeric/grafted hybrids and a chimeric/chimeric standard;

FIG. 14 shows similar graphs for grafted/grafted transfections as well as the chimeric/chimeric standard;

FIG. 17 shows plasmid diagrams for pACtac, pMMR28 and pMRR45;

FIG. 18 shows graphs of CEA binding ELISAs on *E. coli* supernatants containing A5B7 chimeric Fab', and FIG. 19 shows similar graphs for A5B7 grafted Fab'.

DETAILED DESCRIPTION OF SPECIFIC EMBODIMENTS OF THE INVENTION

Example 1

Figure 4:
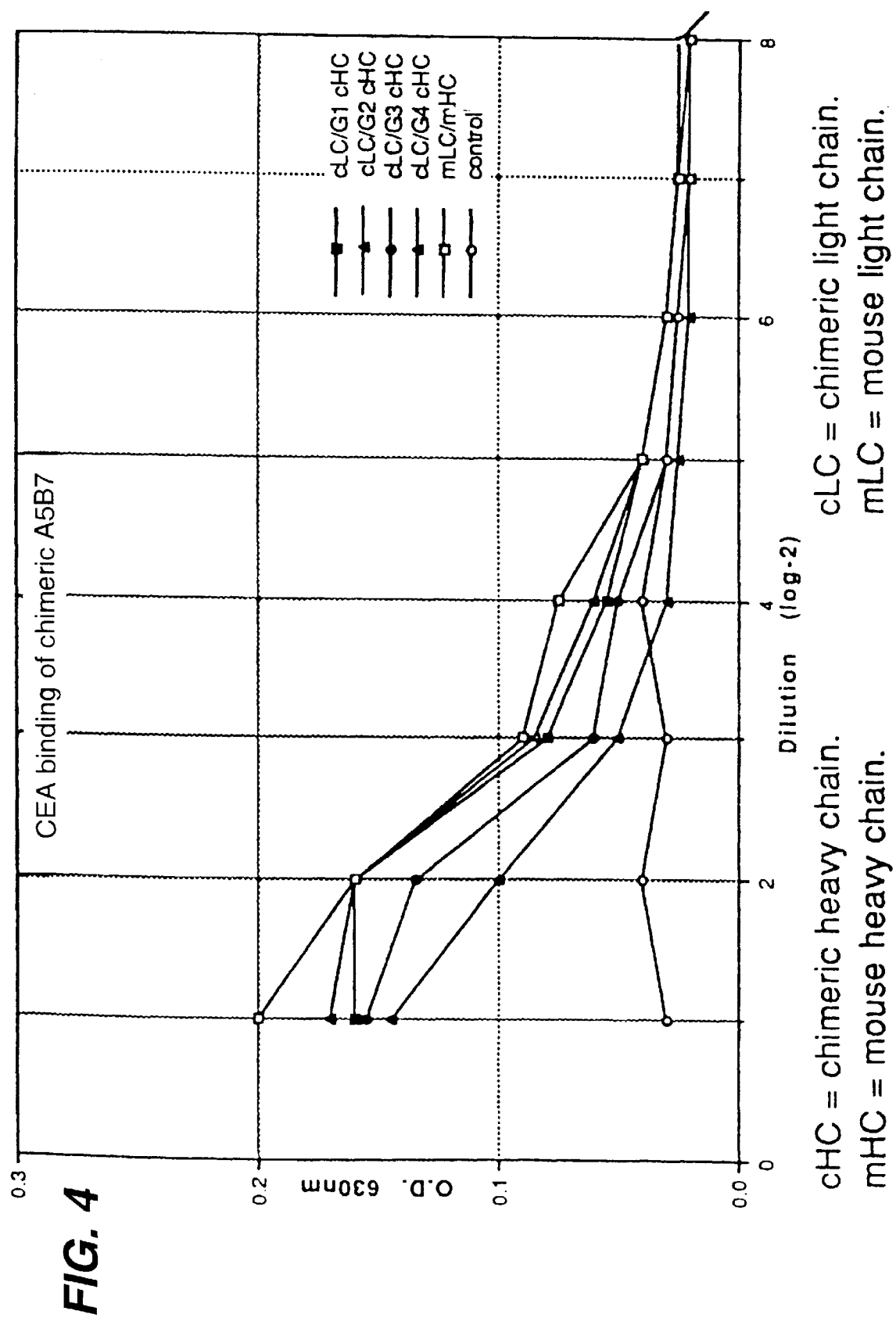
FIG. 4 shows an ELISA analysis of COS-cell transfectant supernatants. The level of antigen-binding capacity in the supernatant of COS-cell transfectants was analysed as described later. Dilution curves were plotted out against the optical density of the colour change.

Molecular Cloning and Sequencing of the A5B7 Heavy and Light Chain cDNAs

Polyadenylated RNA was isolated from the A5B7 hybridoma cell line using the guanidinium isothiocyanate/lithium chloride method (12). Double stranded cDNA was synthesised (16) and a cDNA library was constructed in plasmid pSP64 (17) vector using EcoRI linkers. Two screening probes were synthesised, complementary to mouse immunoglobulin heavy and light chain constant regions. The heavy chain probe was a 19 mer complementary to residues 115–133 in the CH1 domain of the mouse γ1 sequence (18). The light chain probe was a 20 mer complementary to residues 4658–4677 of the genomic mouse CK sequence (19). The probes were radio-labelled at the 5' terminus with [$\gamma^{32}$P] ATP using T4 polynucleotide kinase (Amersham International) and used to screen the cDNA library.

Clones which contained the complete leader, variable and constant regions of both the heavy and light chains were isolated and designated as pBG1 and pBG2. Nucleotide sequence analysis was carried out according to the chain termination procedure (20).

The 950 base pair EcoRI insert in pBG1 was fully sequenced. The EcoRI insert in pBG2 was shown to comprise approximately 1700 base pairs by agarose gel electrophoresis. The variable domain and the 5' region of the CH1 domain were sequenced, as was the 3' end of the clone to confirm the presence of the correct mouse γ1 termination sequences. The DNA and predicted amino acid sequences for the unprocessed variable regions of pBG1 and pBG2 are shown in FIG. 1 and in SEQ ID NOS. 1–4.

With reference to FIG. 1. Panel A shows the sequence coding for the $V_L$ domain and the predicted amino acid sequence. Panel B shows the sequence (SEQ ID NOS. 1 and 2) coding for the $V_H$ domain together with the predicted amino acid sequence. (SEQ ID NOS. 3 and 4) The putative sites of cleavage of the signal peptide are indicated by arrows. Examination of the derived amino acid sequence revealed considerable homology with other characterised immunoglobulin genes, and enabled the extent of the leader, variable and constant domains to be accurately determined. In addition MAb A5B7 was confirmed to be an IgG1 K antibody.

Example 2

Preparation and Testing of Chimeric Antibody Products

A. Construction of Chimeric Mouse-Human Heavy Chain Genes

The construction of vectors containing the human constant region isotype series, pRB18(IgG1), pRB26(IgG2), pRB20 (IgG3) and pRB21 (IgG4) is described in published International Patent Application WO 89/01783. The A5B7 $V_H$ DNA sequence was isolated as a EcoRI-BanI fragment and was ligated to the following linking oligonucleotide to give an EcoRI-HindIII $V_H$ fragment (FIG. 2).

R1120 (SEQ ID NO: 13) 5' GCACCACTCTCACCGTGAGCTC

R1121 (SEQ ID NO: 14) GTGAGAGTGGCACTCGAGTCGA5'

This fragment was ligated to the human HindIII-BamHI containing fragments of the IgG1, 2, 3 & 4 genes cloned in pAT153 to give pBG3, 4, 5 & 6.

The chimeric heavy chain genes were isolated as EcoRI-BamHI fragments from the pAT IgG plasmids and cloned into pEE6 vector (21) cut with EcoRI & BclI, to give plasmids pBG 7,8,9 & 10. The pEE6 plasmid contains the strong promoter/enhancer and transcriptional control element from the human cytomegalovirus immediate early gene (hCMV-IE) inserted into a unique HindIII site upstream of the EcoRI site and is described in detail in published International Patent Application WO 89/01036. In addition, an SV40 origin of replication is provided by the SV40 early promoter fragment which drives as selectable marker gene, a guanine phosphoribosyl transferase gene (gpt) inserted into a unique BamHI site. The plasmid also contains an ampicillin-resistance gene allowing selection and propagation in bacterial hosts.

B. Construction of the Chimeric Mouse-Human Light Chain Gene

A HindIII restriction enzyme site was introduced into the mouse light chain cDNA clone, pBG1 by site-directed mutagenesis (23) using the following oligonucleotide: (SEQ ID NO: 15)

5' TTTGATTTCAAGCTTGGTGC 3'

Introduction of the HindIII site was verified by DNA sequencing. The A5B7 $V_L$ sequence was isolated as an EcoRI/HindIII fragment. It was combined with a HindIII/EcoRI fragment comprising the human Ck constant region and ligated into the unique EcoRI site of pEE6. (FIG. 3). The resulting plasmid pHMC19 also contained the neomycin-resistant gene (neo) under the control of the SV40 early promoter.

C. Transfections and ELISA Analysis of Antibody Production

The four chimeric heavy chain expression constructs described above were transfected together with chimeric light chain into COS-1 cells (24) for transient expression of chimeric products. The cells were left to incubate in DNA-DEAE dextran solution for six hours, then shocked for two minutes with 10% DMSO in HEPES-buffered saline. The cells were washed and incubated in medium containing 10% foetal calf serum for 72 hours.

Following incubation at 37° C. for 72 hours the cell supernatants were analysed by ELISA for heavy and light chain production and binding of antigen.

The medium (500 µl per $10^5$ cells) was removed for ELISA analysis.

To quantify assembled antibody production Microtitre plates were coated with 0.25 µg per well of sheep antibody reactive against human specific epitopes on the heavy or light chains. Supernatants or lysates from transfected COS cells were diluted 1:2 or 1:4 respectively in sample conjugate buffer containing 0.1M Tris-HCl pH 7.0, 0.1M sodium chloride, 0.02% Tween 20 and 0.2% casein. 100 µl of each diluted sample were added to each well and incubated for 1 hour at room temperature with gentle agitation. Following washing six times with wash buffer (phosphate buffered saline containing 0.2% Tween 20, pH 7.2), 100 µl of 1:5000 dilution of standard horseradish peroxidase—conjugated antibody reactive against human specific epitopes were added per well. The plates were incubated for 1 hour at room temperature, and then washed six times with wash buffer. 100 µl of substrate buffer containing 0.1 mg/ml tetramethylbenzidine (TMB), 0.1M sodium citrate, pH 6.0 and 0.005% $H_2O_2$ were added to each well to generate a colour change. The reaction was terminated after 2–3 minutes by adjusting the solution to pH 1.0 with 1.5M sulphuric acid. The optical density was determined at 450 nm for each well by measurement in a Dynatech laboratories MR600 microplate reader. Standard curves were generated using known concentrations of the appropriate human immunoglobulins.

Antigen binding assays were performed in an analogous manner. Microtitre plates were coated with 0.25 µg per well of purified CEA. Following washing six times in wash buffer, samples from COS-cell transfections were added as previously, and the same subsequent procedures carried out, using goat anti-mouse or -human F(ab')$_2$ linked to HRP as the second antibody.

Assembly assays, which detect the presence of associated polypeptide chains, demonstrated the formation of multimers containing at least one heavy and one light chain when both genes were co-transfected. Antigen binding analysis (see above) demonstrated that the chimeric heavy and chimeric light chain co-transfections generated an antibody molecule capable of recognising antigen. The antigen binding ELISA data from one experiment are presented in FIG. 4. These experiments demonstrate that chimerisation of the antibody molecule does not have a significant effect on its antigen recognition capability.

D. Immunoprecipitation of Antibody Molecules from Biosynthetically Labelled COS-Cell Transfectants Following transfection, COS cells were allowed to recover for 24 hours in DMEM containing 10% foetal calf serum. The medium was then replaced with methionine-free DMEM, to which [$^{35}$S] methionine (NEN) had been added at 100 µCi/ml. The cells were metabolically labelled for 48 hours. Analysis of the assembly and secretion of antibody molecules was performed by immunoprecipitation using anti-human F(ab')$_2$ bound to Protein A-Sepharose. Affinity-purified rabbit antibodies against human IgG F(ab')$_2$ were used for immunoprecipitations, following coupling to Protein A—Sepharose. Secreted antibodies were analysed on a SDS-10% PAGE system under reducing and non-reducing conditions. The gel was treated with an autoradiography enhancer, dried and exposed to Fuji RX film.

The antiserum immunoprecipitated proteins with an apparent molecular weight of 55K and 28K, corresponding to the heavy and light immunoglobulin chains respectively. A comparison of immunoprecipitations analysed by reducing and non-reducing SDS-PAGE indicated that the heavy and light chains were assembled as the correct tetrameric molecule.

Example 3

Preparation and Comparison of Chimeric Whole Antibody and Fab' Products

Stable cell lines expressing chimeric whole antibody and Fab' products were established and chimeric whole antibody, Fab', F(ab')$_2$, and synthetically cross-linked DFM (Di Fab' Maleimide) products were prepared and tested.

First of all, however, it was necessary to construct a DNA sequence coding for the chimeric Fab' and vectors for expression of this sequence.

A. Construction of Chimeric Mouse/Human Heavy Chain Gene and Vectors for Fab' Expression The plasmid containing the A5B7 chimeric heavy chain, IgG4, (pBG10) was restricted with BstEll and Bglll. The larger vector fragment containing the hCMV promoter and A5B7 $V_H$ plus the 5' part of CH1 domain was isolated. The plasmid pJA115 (described in International Patent Application WO 89/01974) was restricted with BstE11 and Bglll. A fragment containing the 3' end of CH1 plus the IgG4 hinge containing a cys to ala change was isolated and ligated into the pBG10 vector.

The resulting vector, pBG14, contains the A5B7 Fd' heavy chain IgG4 (cys to ala).

The Assay procedures used in this and subsquent Examples were as follows:

Assembly ELISAs

The ELISA for measuring yields of whole antibodies used microwell plates coated with goat F(ab')$_2$ IgG Fc. Humanised IgG bound following incubation with culture supernatant samples was revealed with horseradish peroxidase (HRP) conjugated murine anti-human kappa chain antibody. Concentrations of chimeric or CDR-grafted whole antibody in samples were interpolated from a calibration curve generated from serial dilutions of purified chimeric A5B7 IgG1.

The ELISA for measuring yields of Fab's used microwell plates coated with murine anti-human IgG Fd. Following incubation with samples bound humanised Fab' was revealed as in the whole antibody assembly ELISA. Concentrations of chimeric or CDR-grafted A5B7 Fab' in samples were interpolated from a calibration curve generated from serial dilutions of purified chimeric A5B7 Fab'.

CEA Binding Assays

The direct CEA binding ELISA used microwell plates coated with CEA. Following incubation with serial dilutions of culture supernatant sample-bound IgG or fragments was revealed as for the assembly ELISA. Binding versus dilution curves were normalised against antibody concentration as determined by the assembly assays.

The competition RIA for anti-CEA activity involved competition of a series of $^{125}$I-labelled murine or chimeric A5B7 IgG1 with humanised IgG or fragments thereof from culture supernatant samples for binding to CEA coated beads. Binding activity was determined by measuring bead associated radioactivity. The assay was calibrated by competition with standard preparations of chimeric or murine A5B7 IgG1 and plotting % bound cpm versus antibody concentration. Interpolated apparent A5B7 concentration of unknowns was normalised by dividing by the assembly assay result to give a specific activity. Finally specific activity was expressed as % relative potency by comparison to that obtained from a positive control chimeric A5B7 culture supernatant produced during the same experiment.

The relative potency of purified murine and chimeric A5B7 Fab' and F(ab')$_2$ fragments and murine IgG was investigated using the competition RIA. In addition, the direct binding ELISA was run in competition mode, by coincubation of the test specimen with murine A5B7 IgG1, for confirmation of relative potency.

Chimeric A5B7 Fab' was purified by ion-exchange chromatography on DEAE-sepharose followed by hydrophobic interaction chromatography on octyl-sepharose. Cross-linking was carried out by the standard one pot procedure using 1,6-bismaleimidohexane as cross-linker, with a 2.2 fold excess of Fab' to cross-linker at 0.9 mg/ml. Due to the small scale of the experiment purification was carried out by HPLC gel filtration (GF-250XL). This yielded an A5B7 chimeric DFM (Di Fab' maleimide) product.

B. Development of CHO Cell Lines expressing Chimeric A5B7 IgG1 and Chimeric IgG4 Fab' delta cys Two types of CHO cell line, amplifiable and non-amplifiable, were developed expressing chimeric A5B7 IgG1 whole antibody and chimeric A5B7 IgG4 FAb' delta cys. The chimeric A5B7 IgG1 whole antibody was used as a standard for assay development and for comparison of chimeric and grafted in biodistribution and therapy studies in tumour-bearing mice.

Non-amplifiable cell lines

Figure 5:
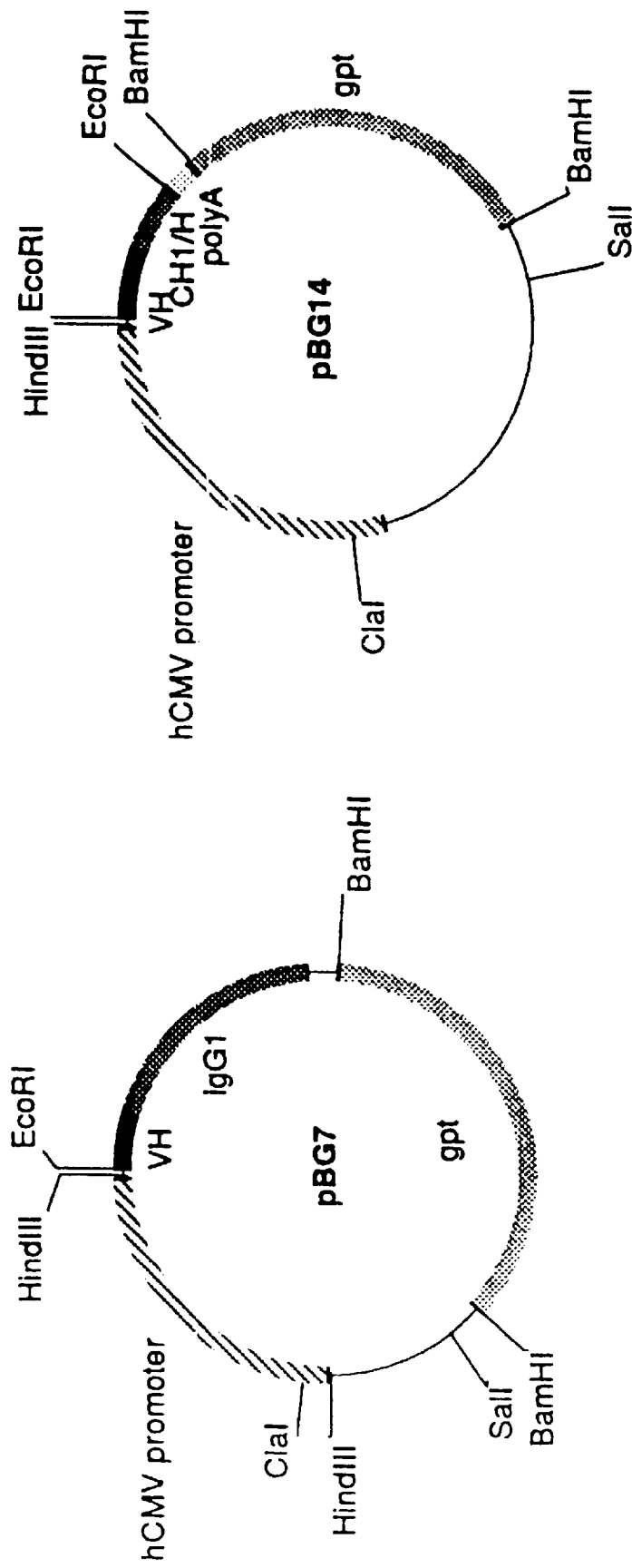
FIG. 5 shows plasmid diagrams for plasmids pBG7, pBG11, pBG14, pHMC19, pHMC20 and pHMC21.

Non-amplifiable cell lines for chimeric whole antibody and Fab' were first constructed. Although such cell lines are relatively low yielding, they are more readily and rapidly prepared and were used for rapid generation of material for development of procedures for purification and for assays. pHMC19 (see Example 2) is a plasmid containing the chimeric A5B7 light chain 3' to the hCMV promoter. This plasmid was transfected into CHO-K1 cells with selection for neomycin resistance and spot assays performed on 30 transfectants with anti-human kappa antibody to identify the best producing clones. Assays with the same antibody on representative cell lines identified a stable cell line, designated HCN1.37, secreting the chimeric A5B7 light chain with a specific production rate of 1–2 $\mu$g/10$^6$ cells. The cell line was retransfected with plasmids pBG7 and pBG14, as described previously, these plasmids carrying the heavy chain genes for chimeric A5B7 IgG1 and chimeric IgG4 Fab' delta cys respectively, in the pEE6hCMV gpt vector (see FIG. 5). Cell lines yielding approximately 16 mg/l chimeric IgG1 (designated HCN1.37/g1.1 and g1.7) and approximately 5 mg/l chimeric Fab' (designated HCN1.37/delta cys3) after purification were identified among these retransfectants by assembly and direct CEA binding assays. These cell lines were used to make test quantities of chimeric whole antibody and Fab'.

Amplifiable Cell Lines

Figure 6:
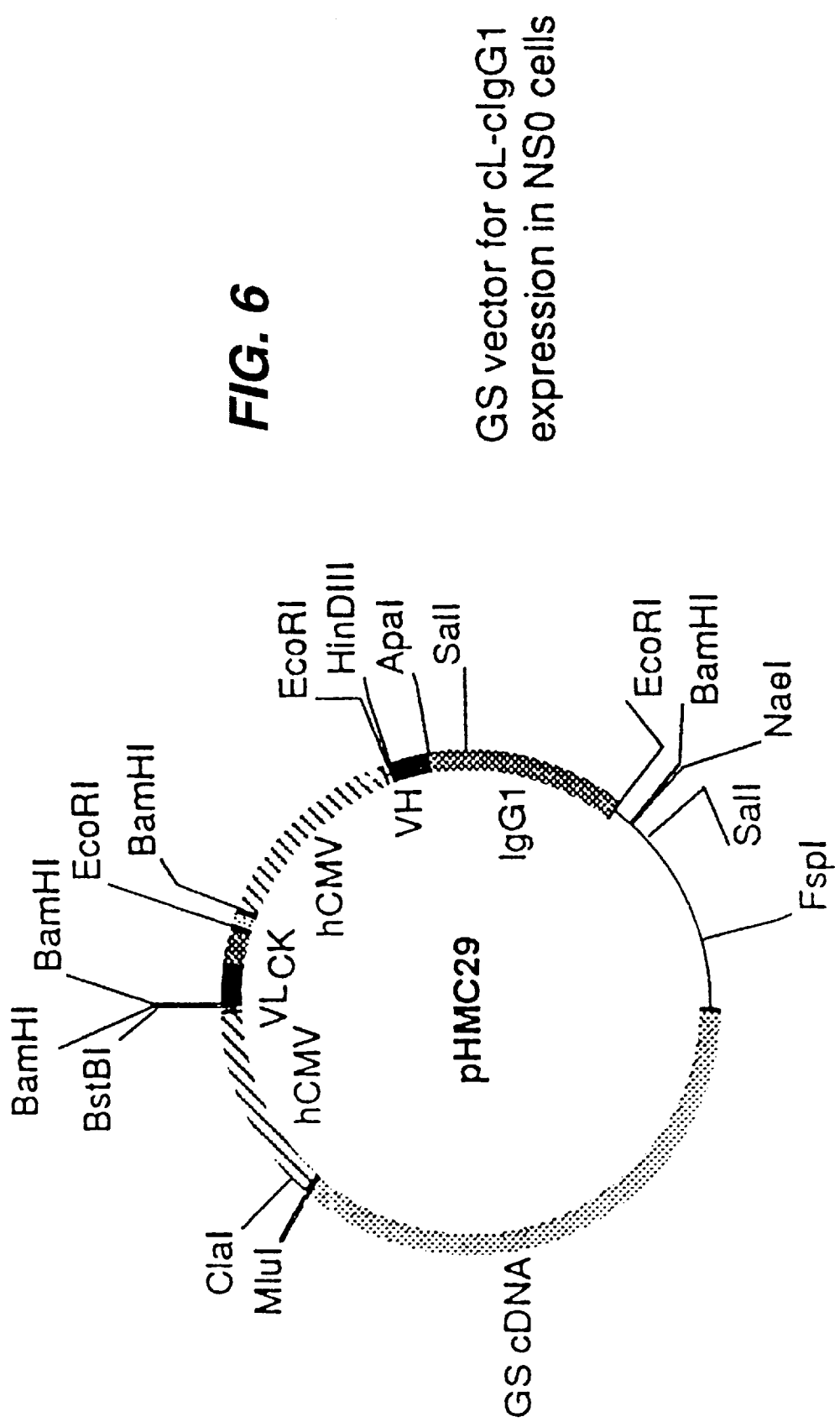
FIG. 6 shows plasmid diagrams for plasmids pHMC29, pHMC30 and pHMC31.

Cell lines capable of amplification by the GS vector system and intended to give yields of chimeric A5B7 Fab' delta cys suitable for eventual manufacture were then constructed. The Cla1-EcoR1 fragment of pBG11 carrying the hCMV promoter and the chimeric A5B7 light chain gene was first cloned between the Cla1 and EcoR1 sites of pEE12 (22) to give plasmid pHMC20 (see FIG. 5). Plasmid pHMC30 (see FIG. 6) carrying the genes for both the chimeric light chain and chimeric IgG4 Fab' delta cys heavy chain was constructed by ligating the large Nae1-Fsp1 fragment of pHMC20 (carrying the light chain gene) to the EcoRV-Fsp1 fragment of pHMC28, a derivative of pBG14 in which the gpt gene has been removed from the BamHI site. pHMC30 is a double gene plasmid suitable for development of an amplifiable cell line, using the mouse myeloma cell line NSO as host cell line, expressing chimeric A5B7 Fab' since it contains the GS cDNA for selection of transfectants. Selection and amplification of transfectants in CHO cells requires expression of the GS minigene rather than the cDNA. A double gene plasmid suitable for development of an amplifiable CHO cell line was constructed by ligating the Mlu1-Fsp1 fragment of pHMC30, carrying both the chimeric light and heavy chain expression units, with the GS minigene containing fragment of pEE14 (25). The resulting plasmid, designated pHMC31 (see FIG. 6), was transfected into CHO-K1 cells with selection on 25 $\mu$M MSX. Specific production rates were determined on these transfectants, and seven chosen for amplification. The specific production rates for these seven transfectants before amplification were as follows (in units of $\mu$g/10$^6$ cells/24 hrs): HC3.36, 1.3; HC3.21, 0.65; HC3.33, 0.65; HC5.19, 0.14; HC5.24, 3.4; HC5.33, 3.7; HC5.39, 0.35. Selection for cells potentially with high copy number of the inserted plasmid sequences was achieved by increasing the MSX concentration to between 100 and 1000 $\mu$M, screening for surviving cell lines and measuring specific production rates. Specific copy number estimates were not done.

C. Purification of Chimeric ASB7 IgG1

Chimeric IgG1 was purified by a modification of the procedure described for B72.3 by Colcher et al (26). CHO cell supernatants were concentrated by spiral cartridge ultrafiltration, then purified by affinity chromatography on protein A Sepharose, with elution at pH3. Reducing and non-reducing SDS-PAGE showed the purified antibody to be fully assembled, with a purity of >95%.

D. Purification and Cross-linking of Chimeric A5B7 Fab'

Chimeric A5B7 Fab' was purified by ion-exchange chromatography DEAE-Sepharose following by hydrophobic interaction chromatography on octyl-Sepharose. CHO cell culture supernatant containing A5B7 Fab' was concentrated ten fold by ultrafiltration and diluted to the original volume with 10 mM tris pH 7.5 to reduce the conductivity to <4 mS. This material was then applied to a column of DEAE-Sepharose fast flow pre-equilibrated with 10 mM tris pH 7.5, and the flow through which contains the Fab' collected. The flow through from the DEAE-Sepharose column was then concentrated by ultrafiltration and made 2M in ammonium sulphate. Any precipitate was removed by centrifugation and the sample then applied to a column of octyl-Sepharose pre-equilibrated with 10 mM tris pH 7.5 containing 2M ammonium sulphate. The Fab' bound to the column and was washed with equilibration buffer and eluted by decreasing the ammonium sulphate concentration to 1M. The elute was then dialysed into 100 mM sodium acetate/citrate pH6 and concentrated by ultrafiltration.

The purified Fab' was cross-linked by firstly generating a free thiol at the hinge followed by cross-linking with 1,6-bismaleimidohexane. Partial reduction to generate a free thiol was achieved by incubation of the Fab' with 4.5 mM β-mercaptoethylamine for 30 minutes at 37° C. The reducing agent was then removed by desalting on a column of Sephadex G-25 and the reduced Fab' immediately cross-linked by incubation with 1,6-bismaleimidohexane at a molar ratio of 1:2.2 bismaleimidohexane:Fab' with a Fab' concentration of 0.9 mg/ml. After overnight incubation at 37° C. the cross-linked material was purified by HPLC gel filtration using a DuPont Zorbax GF-250XL column in 0.2M phosphate pH 7.0. The cross-linking yield was approximately 58%.

Figure 7:
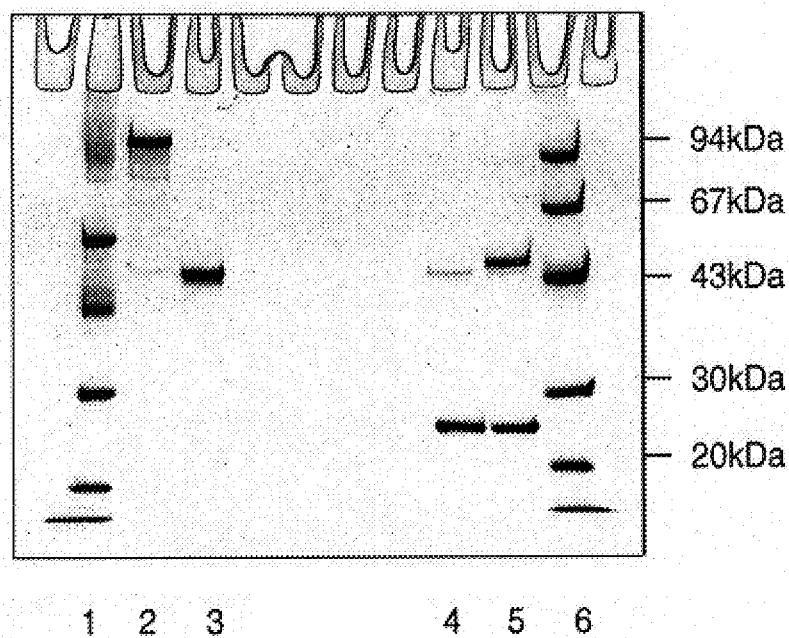
FIG. 7 shows a SDS-PAGE gel of chimeric FAb' and chimeric DFM products under both reducing and non-reducing conditions.

The purified Fab' and cross-linked di-Fab (DFM) were analysed by SDS-PAGE under both reducing and non-reducing conditions (FIG. 7). The purified Fab' ran as expected with a molecular weight of approximately 50 KDa under non-reducing conditions which reduced to Fd' and light chains at 25 KDa. The purified cross-linked di-Fab revealed the expected molecular weight for the non-reduced dimer of 100 KDa which reduced to cross-linked Fd' at approximately 50 KDa and light chain at approximately 25 KDa.

E. Antigen Binding Activity of Chimeric A5B7 IgG1, Fab' and DFM

The relative potencies of murine and chimeric IgGs and fragments were measured by the competition RIA. The results are given in Table 1. All the bivalent species—including the chimeric DFM—gave potency equivalent to that of murine A5B7 IgG. The murine Fab' rendered monovalent by alkylation, showed a tenfold reduced potency, as would be predicted by avidity considerations. The monovalent chimeric Fab', however, displayed an intermediate potency. Measurements of binding activity on the same samples using the direct binding ELISA in competition mode gave very similar results, with the chimeric Fab' again showing an intermediate potency. Since the chimeric Fab' was not alkylated its increased binding activity compared to the murine Fab' is likely to be due to some degree of antigen induced dimerisation.

TABLE 1

Relative potencies of various A5B7 constructs by competitive RIA

| Construct | % Relative Potency |
|---|---|
| Chimeric IgG | 100 |
| Murine IgG | 93 + 23 |
| Chimeric DFM | 104 + 28 |
| Murine F(ab)$_2$ | 97 + 22 |
| Chimeric Fab' | 20 + 15 |
| Murine Fab' | 8 + 5 |

Example 4

Humanised, CDR-grafted versions of A5B7 were also prepared.

Construction and Expression of CDR-grafted A5B7 Genes

FIG. 1 shows the DNA and amino acid sequences (SEQ ID NOS: 1–4) of the $V_L$ and $V_H$ domains for A5B7. CDR-grafted $V_H$ and $V_L$ domains were designed substantially as described in International Patent Application No. PCT/GB 90/02017. The amino acid sequence of A5B7 $V_H$ (SEQ ID NO: 4) shows considerable homology to the consensus sequence of the human $V_H$ III subgroup, as defined by Kabat et al, (15), while the $V_L$ sequence (SEQ ID NO: 2) shows considerable homology to those of the human VII and III subgroups. The human framework sequences available within these subgroups are: LAY($V_H$:$V_L$), POM ($V_H$:$V_L$), KOL ($V_H$):REI($V_L$), KOL($V_H$):EU($V_L$), TUR ($V_H$): REI($V_L$), TUR($V_H$):Eu($V_L$), TEI($V_H$):REI($V_L$), TEI ($V_H$): EU($V_L$). Of these LAY was chosen as the human framework because it has the highest homology to A5B7 and also the potential advantage of matched $V_H$ and $V_L$ chains. CDR sequences and other residues potentially important for antigen binding were identified as described in International Patent Application No. PCT/GB 90/02017, and for each V domain two constructs were assembled. The first constructs, gL1 (SEQ ID NOS. 5 and 6) and gH1 (SEQ ID NOS. 9 and 10) contain murine sequences in the CDRs and at other positions predicted to be important for antigen binding and at which human and A5B7 sequences differ. The gL1 light chain (SEQ ID NOS. 5 and 6) has murine CDRs at residues 24–34 (CDR1), 50–56 (CDR2) and 89–97 (CDR3) and additional murine residues within the frameworks at residues 1, 2, 3, 4, 46 and 71. The gH1 heavy chain (SEQ ID NOS. 9 and 10) has murine CDRs at residues 26–35 (CDR1), 50–65 (CDR2) and 95–102 (CDR3) and additional murine residues within the frameworks at residues 1, 48, 49, 72, 73, 76 and 93.

The second constructs, gL2 (SEQ ID NOS. 7 and 8) and gH2 (SEQ ID NOS. 11 and 12) are more conservative, containing the murine sequences present in the first constructs together with three extra murine residues for $V_L$ and two for $V_H$. For gL2 (SEQ ID NOS. 7 and 8) these residues (positions 21, 47 and 73 on the Kabat numbering system) are potentially involved in packing of the domain. For gH2 (SEQ ID NOS. 11 and 12) the extra murine residues are at positions (82b and 86) where LAY has amino acids which are unusual for human $V_H$ sequences and where A5B7 has residues of more common occurrence in human $V_H$s.

FIGS. 8, 9, 10 and 11 show the DNA and amino acid sequences of gL1, gL2, gH1 and gH2 respectively (SEQ ID NOS. 1–12 respectively). In these Figures single letter underlining in the amino acid sequences indicate a residue in the framework region which has been changed to the corresponding murine residue. Also in these Figures solid single line underlining of the amino acid sequences indicates the CDR residues. These DNA sequences were assembled from oligonucleotides (indicated by double line underlining in the respective Figure) by the PCR overlap-assembly procedure, using a Polymerase Chain Reaction (PCR) procedure, using oligonucleotides of approximately 80 bases alternating on the sense and anti-sense strands. The oligonucleotides overlapped by 20 bases, such that annealing led to the formation of partially double stranded molecules. The gaps were filled in by Taq polymerase and the double stranded material amplified by PCR using short oligonucleotides corresponding to the sequence of the 5' end of each strand as amplifiers. The amplified fragments were digested with appropriate restriction enzymes to expose the restriction sites for cloning.

Figure 12:
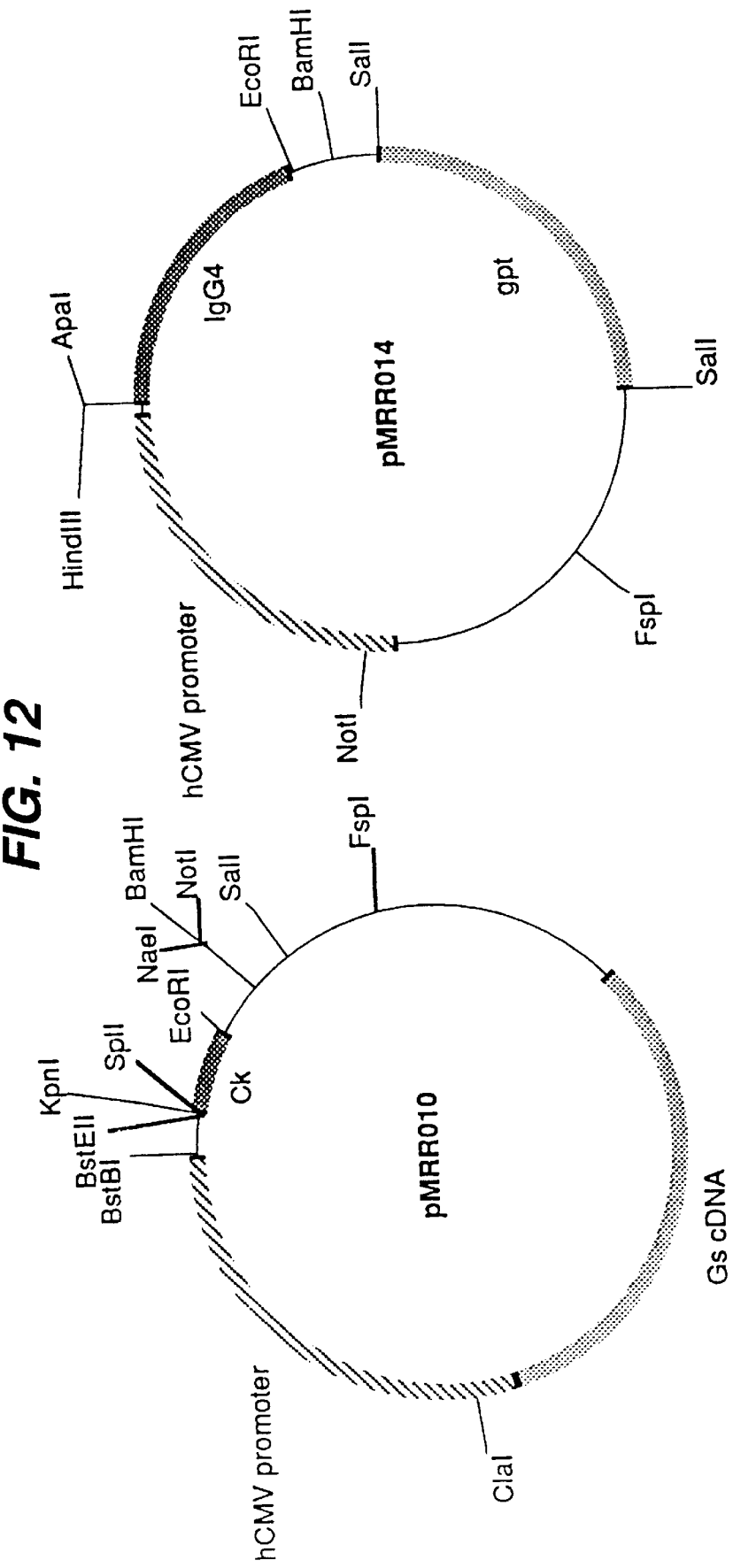
FIG. 12 shows plasmid diagrams for plasmids pMRR010, pMRR014, pAL43, pAL44, pAL45 and pAL46.

Amplified fragments of the appropriate size were digested with HindIII and ApaI for $V_H$, and BstBI and SplI for $V_L$ to expose the cloning sites. The $V_H$ fragments were cloned into the expression vector pMRR014 and the $V_L$ fragments into pMRR010. pMRR010 and pMRR014 are hCMV expression vectors designed to accept humanised V regions so as to be readily expressed transiently in CHO or COS cells and then readily to be reconstructed to give a single vector capable of stable expression and gene amplification in NSO cells. This gave plasmids pAL43 (for gL1), pAL44 (gL2), pAL45 (gH1) and pAL46 (gH2) as shown in FIG. 12. These plasmids contain the full length CDR-grafted antibody genes (IgG1 for heavy chain, kappa for light chain) in a configuration suitable for expression in CHO cells. Clones containing the correct sequence were identified by DNA sequencing.

In order to assess the CEA binding activity of the grafted chains co-expression, experiments in a transient CHO cell system were first performed with chimeric partners. Thus pAL43 and pAL44 were co-transfected into the CHO L761 h cell line (27) together with the chimeric A5B7 heavy chain expression plasmid pBG7, while pAL45 and pAL46 were co-transfected with the light chain expression plasmid pBG11. Co-transfections of pBG7 and pHMC19 were also performed to provide a chimeric/chimeric standard against which to compare activity of the chimeric/grafted hybrids. FIG. 13 shows the results of direct CEA binding ELISAs on the crude supernatants resulting from these transfections, and indicates that all the grafted/chimeric hybrids show binding activity similar to that of the chimeric/chimeric standard. Considerable variation was observed between the various hybrids in the yields of antibody. This variation was also very apparent when grafted/grafted co-transfections were performed. Indeed, the yields observed for gL1/gH1 and gL2/gH1 were too low to permit reliable estimates of CEA binding activity. Both the gL1/gH2 and gL2/gH2 combinations, however, bound CEA at approximately 60% as well as the double chimeric antibody in the direct binding assay (see FIG. 14). Competition RIAs were also performed on the crude CHO cell supernatants for gL1/gH2 and gL2/gH2. The results, shown in Table 2, show that these grafted variants displayed approximately 42% and 47% respectively of the potency of the chimeric in these more stringent assays, with gL2/gH2 showing slightly greater potency than gL1/gH2.

TABLE 2

Estimates of Anti-CEA Activity in Transfected CHO Cell Supernatants for Grafted Variants of A5B7 by Competition RIA

| | Undiluted | |
| --- | --- | --- |
| Construct | Specific activity | relative potency |
| Chimeric A5B7 | 1.17 | 100 ± 6 |
| Grafted A5B7 gL1/qH2 | 0.49 | 42 ± 4 |
| Grafted A5B7 gL2/gH2 | 0.55 | 47 ± 3 |

Example 5

Similarly CDR-grafted A5B7 Fab' genes were constructed and expressed.

Figure 15:
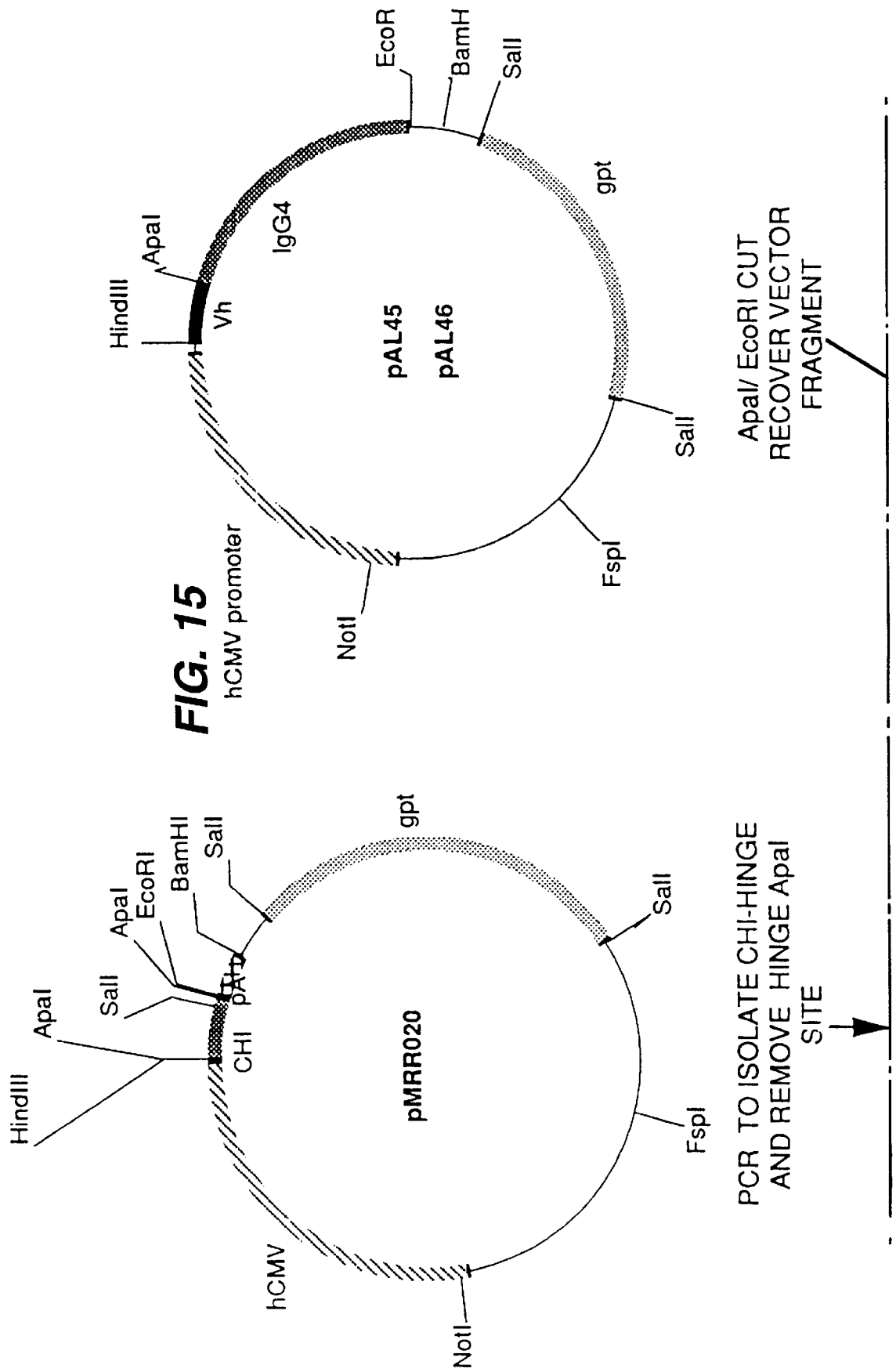
FIG. 15 shows plasmid diagrams of plasmids pMRR020, pAL45, pAL46, pAL49 and pAL50 indicating the derivation of the latter two plasmids.

A. Construction of CDR-grafted A5B7 Fab' Genes pMRR020 is a pEE6 gpt expression plasmid with restriction sites such that coding sequences of the human IgG4 CH1 and delta cys (i.e. single cysteine variant) hinge domains (see FIG. 15). A fragment containing these two domains was isolated by performing a PCR reaction on pMRR020 using oligonucleotide R1053 as the forward primer and R2371 as the back primer as shown below.

R1053 (SEQ ID NO: 16) 5' GTCGACAGACTAACAGACTGT-TCC 3'

R2371 (SEQ ID NO:17) 5' ATGATCAATGAATTCAT-CATGGGGCTGATGGGCACGGGGGACCATATTTGGACTC 3'

Use of the latter primer results also in the removal of the inconvenient Apa1 site in the hinge coding region. The PCR reaction produced a fragment of 320 bp, which was cloned into pAL45 and pAL46 to give pAL49 and pAL50 respectively (FIG. 15) carrying the full length CDR-grafted Fd delta cys genes. The CH1 and hinge domains and the cloning junction regions were sequenced to confirm the absence of secondary mutations.

Figure 16:
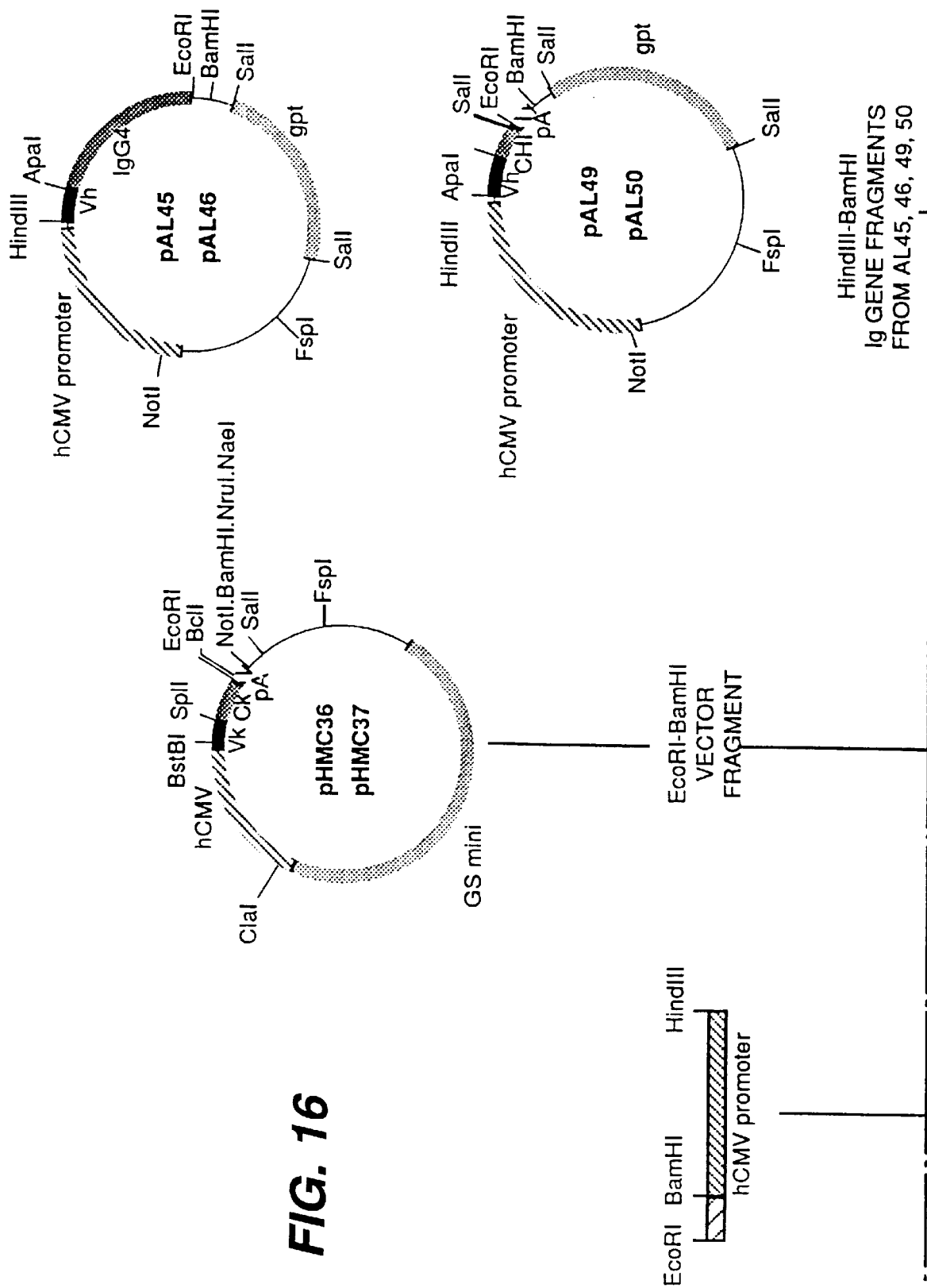
FIG. 16 shows plasmid diagrams of various plasmids indicating the derivation of plasmids pHMC43, pHMC44, pAL53 and pAL54.

B. Development of CHO Cell Lines Expressing CDR-grafted A5B7 IgG1 Whole Antibody and CDR-grafted A5B7 IqG4 Fab' delta cys genes To make stable cell lines expressing CDR-grafted IgG1 whole antibody and CDR-grafted Fab' the gL1 and gL2 genes were first isolated as Cla1-EcoR1 fragments from pAL43 and pAL44 and cloned into the vector pMRR017, a derivative of pEE14 with a useful poly-linker inserted at the BamHI site to give plasmids pHMC36 and pHMC37 respectively (see FIG. 16). The gH1(IgG1), gH2(IgG1), gH1(Fd delta cys) and gH2(Fd delta cys) genes were isolated as Hindlll-BamH1 fragments from pAL45, 46, 49 and 50 respectively and cloned along with an EcoR1-Hindlll fragment carrying the SV40 polyA and hCMV promoter between the EcoR1 and BamH1 sites of pHMC36 to give plasmids pHMC43 (gL1-gH1), pHMC44(gL1-gH2), pAL53 (gL1-gH1Fd delta cys) and pAL54 (gL1-gH2Fd delta cys). These GS double gene expression plasmids (see FIG. 16) were transfected into CHO-K1 cells to give CDR-grafted IgG1 whole antibody and CDR-grafted Fab' producing cell lines substantially as described in previous Examples.

Example 6

Production of A5B7 antibody fragments in E. coli

Chimeric and CDR-grafted A5B7 Fab' fragments (the gL1gH2 CDR-grafted variant was used) were also expressed in an E. coli secretion system, this being the preferred expression host for large scale production of antibody fragments.

For expression/secretion in E. coli the natural signal sequences of the A5B7 heavy and light chains were first replaced with the signal sequence of the E. coli outer membrane protein ompA (Movva et al, 28). A 92 base pair fragment encoding the ompA signal sequence and including the ompA translation initiation region was assembled from oligonucleotides and cloned into the phagemid vector pSK+ (from Stratagene Cloning Systems) between the XhoI and Hindlll sites. The DNA and amino acid sequence (SEQ ID NOS. 18, 19, and 20) of the 92 base pair fragment were as follows:

```
                         met lys lys thr ala ile ala ile ala val ala
5 TCGAGTTCTAGATAACGAGGCGTAAAAAATGAAAAAGACAGCTATCGCGATTGCAGTGGCA
3         CAAGATCTATTGCTCCGCATTTTTTACTTTTTCTGTCGATAGCGCTAACGTCACCGT leu ala gly phe ala thr val ala gln ala
CTGGCTGGTTTCGCTACCGTAGCGCA        3
GACCGACCAAAGCGATGGCATCGCGTTCGA    5
```

A clone shown by DNA sequencing to carry the above sequence in pSK+ was designated pSKompA.

For the chimeric A5B7 light chain a 650 base pair Sac1-EcoR1 fragment encoding most of $V_L$ and all of C kappa was isolated from pHMC19. A precise fusion of the chimeric Light chain to the ompA signal sequence was made by ligating this Sac1-EcoR1 fragment into pSKompA digested with Hindlll and EcoR1 together with a 54 base pair Hindlll-Sacl fragment assembled from oligonucleotides and comprising the DNA sequence encoding the 3' region of the ompA signal sequence and the 5' region of A5B7 $V_L$. The sequence of the 51 base pair fragment was as follows:

(SEQ ID NO: 21) 5' AGCTCAAACTGTTCTCTCCCAGTCTC-
   CAGCAATCCTGTCTGCATCTC 3'

(SEQ ID NO: 22) 3' GTTTGACAAGAGAGGGTCAGAG-
   GTCGTTAGGACAGACGTAGAGGTCC 5'

A clone containing the correct sequence was identified by DNA sequencing and designated pSKompA-cLc.

For the chimeric A5B7 heavy chain a 580 base pair Ava11-EcoR1 fragment encoding most of $V_H$ and all of the CH1 and (delta cys) hinge domains was isolated from pBG14. A precise fusion of the chimeric heavy chain to the ompA signal sequence was made by ligating the Ava11-EcoR1 fragment into pSKompA digested with Hindlll and EcoR1 together with a 120 base pair fragment assembled from oligonucleotides and comprising the DNA sequence encoding the 3' end of the ompA signal sequence and the 5' region of $V_H$. The sequence of the 120 base pair fragment was as follows:

(SEQ ID NO:23) 5' AGCTGAGGTGAAGCTTGTGGAGTCTGGAGGAGGGTTGGTACAGCCTGGGGGTTCTCTGA
(SEQ ID NO:24) 3'     CTCCACTTCGAACACCTCAGACCTCCTCCGAACCATGTCGGACCCCCAAGAGACT

GACTCTCCTGTGCAACTTCTGGGTTCACCTTCACTGATTACTACATGAACTGG        3'
CTGAGAGGACACGTTGAAGACCCAAGTGGAAGTGACTAATGATGTACTTGACCCAGG  5'

A clone containing the correct sequence was identified by DNA sequencing and designated pSKompA-cFd.

For expression of the chimeric Fab' the ompA-cLc fusion was then removed from pSKompA-cLc on a Xho1-EcoR1 fragment and cloned into the expression vector pACtac digested with Sa11 and partially with EcoR1 (see FIG. 17). pACtac was constructed by replacing the Amp$^r$ selectable marker and pUC18-derived replication functions of the expression plasmid, pTTQ9 (Amersham International) with the Cm$^r$ selectable marker and replication functions of pACYC184 (Chang & Cohen, 1978, J. Bacteriol. 134: 1141–1156). (Partial EcoR1 digestion was required because pACtac contains a second EcoR1 site, in the Cm$^r$ gene.) A plasmid with ompA-cLc inserted adjacent to the tac promoter was identified by restriction mapping and DNA sequencing and designated pMRR024.

The ompA-cFd fragment was removed from pSKompA-cFd as a Xho1-Sma1 fragment and cloned into pSP73 (Promega Corporation) digested with Sal1 and Pvu11, to give a plasmid designated pMRR027. The ompA-cFd fusion was then removed from pMRR027 as an EcoR1 fragment, which was cloned into pMRR024 partially digested with EcoR1. A clone carrying ompA-cFd oriented for transcription from the tac promoter (along with ompA-cLc) was identified by restriction mapping and DNA sequencing and designated pMRR028.

pMRR028 was transformed into *E. coli* strain W3110 (ATCC strain 27325). Strain W3110 (pMRR028) was grown in a 1.5 L fermenter in medium containing chloramphenicol to maintain selection for retention of the plasmid. At a culture O.D 600 nm of 10 expression of the A5B7 Fab' genes from the tac promoter was induced by adding the inducer IPTG to a final concentration of 1 mM. Direct CEA binding assays were performed on crude culture supernatant samples taken from this culture at time points 0, 3, 4, 5, 6, 7 and 8 hours after induction. The results of these assays, together with that of a chimeric A5B7 Fab' standard made and purified from mammalian cells are shown in FIG. 18. They demonstrate the accumulation of active chimeric A5B7 Fab' in the *E. coli* culture medium. SDS-PAGE analysis on the same crude culture medium samples revealed proteins with mobility of the size expected for Fab' heavy and light chains. N-terminal protein sequencing on these proteins revealed the N-terminal amino acid sequences of mature A5B7 heavy and light chains, showing that the ompA signal sequence had been accurately cleaved from both. Estimates (by OD 280 nM measurements and by SDS-PAGE) for the chimeric Fab' in the *E. coli* culture medium were performed: the results suggested yields in excess of 30 mg/L after purification.

For the CDR-grafted A5B7 Fab' light chain a 620 base pair Hph1-EcoR1 fragment encoding most of $V_L$ for the gL1 variant and all of C kappa was isolated from pAL43. A precise fusion of the grafted light chain to the ompA signal sequence was made by ligating the Hph-EcoR1 fragment into pSKompA digested with Hindlll and EcoR1 together with a 62 base pair fragment assembled from oligonucleotides and encoding the 3' end of the ompA signal sequence and the 5' end of the CDR-grafted $V_L$. The sequence of the synthetic fragment was as follows: (SEQ ID NOS. 25 and 26)

AGCTCAGACTGTACTCACTCAGAGTCCAAGTAGTCTCAGT
GTAAGTGTAGGTGATAGGGTAAGTCTGA-
CATGAGTGAGTCTCAGGTTCATCAGAGT-
CACATTCACATCCACTATCCCAT

A clone carrying the correct sequence was identified by DNA sequencing and designated pMRR034.

For the CDR-grafted A5B7 Fab' heavy chain gene a 720 base pair Pvu11-EcoR1 fragment encoding most of $V_H$ for the gH2 variant and all of CH1 and the (delta cys) hinge domains was isolated from pAL50. A precise fusion of this grafted H chain to the ompA signal sequence was made by ligating this Pvu11-EcoR1 fragment into pSKompA digested with Hindlll and EcoR1 together with a very short fragment assembled from oligonucleotides and encoding the 3' end of the ompA signal and the 5' end of the CDR-grafted $V_H$. The sequence of the short adaptor fragment was as follows:

(SEQ ID NO:27) 5' AGCTGAGGTGCAG 3'

3' CTCCACGTC 5'

A clone containing the correct sequence was identified by DNA sequencing and designated pMRR037.

For expression of CDR-grafted Fab' the ompA-gL1 fusion was taken from pMRR034 as a Xho1-EcoR1 fragment and cloned into pACtac digested with Sall and partially with EcoR1. A clone carrying ompA-gL1 adjacent to the tac promoter was identified by restriction mapping and DNA sequencing and designated pmRR038. The ompA-gH2 fusion was then taken from pMRR037 as a Xho1-Sma1 fragment and cloned into pSP73 doubly digested with Pvu11 and EcoR1 to give a plasmid designated pMRR041. The ompA-gH2 fusion was then removed from pMRR041 as an EcoR1 fragment and cloned into pMRR038 partially digested with EcoR1. A clone carrying the ompA-gH2 fusion oriented for transcription from the tac promoter (along with ompA-gL1) was identified by restriction mapping and DNA sequencing and designated pMRR045.

pMRR045 was transformed into *E. coli* strain W3110 and the W3110 (pMRR045) strain resulting was grown in a 1.5 L fermenter. Expression of the CDR-grafted Fab' genes was induced as described above for the chimeric Fab' genes. Crude culture supernatant samples from this culture at time points 1, 4, 5, 6, 11 and 22 hours after induction were used in direct CEA binding assays and yield estimates. The results of the CEA binding assays are given in FIG. 19 and show the accumulation of material active in antigen binding. SDS-PAGE analysis of these supernatant samples demonstrated the presence of proteins of the size expected, and suggested yields in excess of 30 mg/L.

REFERENCES

1. Kohler & Milstein, Nature, 265, 495–497, 1975.
2. Begent et al, Br. J. Cancer, 62: 487 (1990).
3. Verhoeyen et al, Science, 239, 1534–1536, 1988.
4. Riechmann et al, Nature, 332, 323–324, 1988.
5. Queen et al, Proc. Natl. Acad. Sci., USA, 86: 10029–10033, 1989 and WO 90/07861.
6. Ehrlich, P., Collected Studies on Immunity, 2, John Wiley & Sons, New York, 1906.
7. Levy & Miller, Annm. Rev. Med., 34, 107–116, 1983.
8. Schlom & Weeks, Important Advances in Oncology, 170–192, Wippincott, Philadelphia, 1985.
9. Sahagan et al, J. Immunol., 137, 3, 1066–1074. 1986
10. Nishimura et al, Cancer Res., 47 999–1005, 1987.
11. Harwood et al, Br. J. Cancer, 54, 75–82, 1986.
12. Maniatis et al, Molecular Cloning, Cold Spring Harbor, N.Y., 1982.
13. Primrose and Old, Principles of Gene Manipulation, Blackwell, Oxford, 1980.
14. Jones et al, Nature, 54, 75–82, 1986.
15. Kabat et al, (1987), Sequences of Proteins of Immunological Interest, US Department of Health and Human Services, NIH, USA, and Wu, T. T., and Kabat, E. A., J. Exp. Med., 132, 211–250, 1970.
16. Gubler and Hoffman, Gene, 25, 263–269, 1983.
17. Melton et al, Nucl. Acids Res., 12, 7035–7056, 1984.
18. Honjo et al, Cell, 18, 559–568, 1979.
19. Max et al, J. Biol. Chem., 256, 5116–5120, 1981.
20. Sanger et al, PNAS, 74, 5463–5467, 1977.
21. Stephens and Cockett, Nucl. Acids Res., 17, 7110, 1989
22. Krawinkel and Rabbits, EMBO J., 1, 403–407, 1982.
23. Kramer et al, Nucl. Acids Res., 12, 9441–9446, 1984.
24. Whittle et al, Prot. Eng., 1, 6, 499–505, 1987.
25. Bebbington, C. R., "Expression of Antibody Genes in Non-Lymphoid Mammalian Cells", *Methods,* 2: 136–145, 1991.
26. Colcher et al, (1989), Cancer Res., 49, 1738–1745.
27. Cockett et al, Nucl. Acids. Res., 19, 319–325. 1991
28. Movva et al, J. Bio. Chem., 255, 27–29, 1980.

We claim:

1. An antibody molecule having specificity for carcinoembryonic antigen comprising a composite heavy chain and a complementary light chain, said composite heavy chain having a variable domain comprising the amino acid sequence of SEQ ID NO: 10.

2. An antibody molecule having specificity for carcinoembryonic antigen comprising a composite heavy chain and a complementary light chain, said composite heavy chain having a variable domain comprising the amino acid sequence of SEQ ID NO: 12.

3. An antibody molecule having specificity for carcinoembryonic antigen comprising a composite light chain and a complementary heavy chain, said composite light chain having a variable domain comprising the amino acid sequence of SEQ ID NO: 6.

4. An antibody molecule having specificity for carcinoembryonic antigen comprising a composite light chain and a complementary heavy chain, said composite light chain having a variable domain comprising the amino acid sequence of SEQ ID NO: 8.

5. An antibody molecule having specificity for carcinoembryonic antigen comprising a composite light chain and a composite heavy chain, said composite light chain having a variable domain comprising an amino acid sequence selected from SEQ ID NOs: 6 and 8 and said composite heavy chain having a variable domain comprising an amino acid sequence selected from SEQ ID NOs: 10 and 12.

6. The antibody molecule of claim 1, 2, 3, 4, or 5, wherein said antibody molecule is selected from the group consisting of a complete antibody molecule, Fab, Fab', (Fab')$_2$, Fv, and a single chain antibody.

7. The antibody molecule of claim 1, 2, 3, 4, or 5, further wherein said molecule has an effector or reporter molecule attached thereto.

8. The antibody molecule of claim 1, 2, 3, or 4 wherein the complementary chain is a chimeric chain.

9. A therapeutic or diagnostic composition comprising the antibody molecule of claim 1, 2, 3, 4, or 5 in combination with a pharmaceutically acceptable excipient, diluent, or carrier.

* * * * *

UNITED STATES PATENT AND TRADEMARK OFFICE
CERTIFICATE OF CORRECTION

PATENT NO.    : 5,877,293
DATED         : March 2, 1999
INVENTOR(S)   : Adair et al.

It is certified that error appears in the above-identified patent and that said Letters Patent is hereby corrected as shown below:

Item [57] Abstract,
Line 6, please delete "(A5B7 MAB)" and insert therefor -- (A5B7 MAb) --;

Columns 15 & 16,
Example 6, line 2 of 92 base pair fragment, please delete "5" and insert therefor -- 5` --; line 3, please delete "3" and insert therefor -- 3` --; line 5 please delete "3" and insert therefor -- 3` --; line 6, please delete "5" and insert therefor -- 5`--.

Signed and Sealed this

Ninth Day of October, 2001

*Attest:*

NICHOLAS P. GODICI
*Attesting Officer*       Acting Director of the United States Patent and Trademark Office

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 387 base pairs
        ( B ) TYPE: nucleic acid
        ( C ) STRANDEDNESS: double
        ( D ) TOPOLOGY: linear ( v i i ) IMMEDIATE SOURCE:
        ( B ) CLONE: A5B7 light chain Vl domain ( i x ) FEATURE:
        ( A ) NAME/KEY: CDS
        ( B ) LOCATION: 1..387

( x i ) SEQUENCE DESCRIPTION: SEQ ID NO:1:

```
ATG  GAT  TTT  CAA  GTG  CAG  ATT  TTC  AGC  TTC  CTG  CTA  ATC  AGT  GCT  TCA        48
Met  Asp  Phe  Gln  Val  Gln  Ile  Phe  Ser  Phe  Leu  Leu  Ile  Ser  Ala  Ser
 1              5                        10                       15

GTC  ATA  ATG  TCC  AGA  GGA  CAA  ACT  GTT  CTC  TCC  CAG  TCT  CCA  GCA  ATC        96
Val  Ile  Met  Ser  Arg  Gly  Gln  Thr  Val  Leu  Ser  Gln  Ser  Pro  Ala  Ile
               20                       25                       30

CTG  TCT  GCA  TCT  CCA  GGG  GAG  AAG  GTC  ACA  ATG  ACT  TGC  AGG  GCC  AGC       144
Leu  Ser  Ala  Ser  Pro  Gly  Glu  Lys  Val  Thr  Met  Thr  Cys  Arg  Ala  Ser
               35                       40                       45
```

| | | | | | | | | | | | | | | | | |
|---|---|---|---|---|---|---|---|---|---|---|---|---|---|---|---|---|
| TCA | AGT | GTA | ACT | TAC | ATT | CAC | TGG | TAC | CAG | CAG | AAG | CCA | GGA | TCC | TCC | 192 |
| Ser | Ser | Val | Thr | Tyr | Ile | His | Trp | Tyr | Gln | Gln | Lys | Pro | Gly | Ser | Ser | |
| | 50 | | | | 55 | | | | | 60 | | | | | | |
| CCC | AAA | TCC | TGG | ATT | TAT | GCC | ACA | TCC | AAC | CTG | GCT | TCT | GGA | GTC | CCT | 240 |
| Pro | Lys | Ser | Trp | Ile | Tyr | Ala | Thr | Ser | Asn | Leu | Ala | Ser | Gly | Val | Pro | |
| 65 | | | | 70 | | | | | 75 | | | | | 80 | | |
| GCT | CGC | TTC | AGT | GGC | AGT | GGG | TCT | GGG | ACC | TCT | TAC | TCT | CTC | ACA | ATC | 288 |
| Ala | Arg | Phe | Ser | Gly | Ser | Gly | Ser | Gly | Thr | Ser | Tyr | Ser | Leu | Thr | Ile | |
| | | | | 85 | | | | | 90 | | | | | 95 | | |
| AGC | AGA | GTG | GAG | GCT | GAA | GAT | GCT | GCC | ACT | TAT | TAC | TGC | CAA | CAT | TGG | 336 |
| Ser | Arg | Val | Glu | Ala | Glu | Asp | Ala | Ala | Thr | Tyr | Tyr | Cys | Gln | His | Trp | |
| | | | 100 | | | | | 105 | | | | | 110 | | | |
| AGT | AGT | AAA | CCA | CCG | ACG | TTC | GGG | GGA | GGC | ACC | AAG | CTG | GAA | ATC | AAA | 384 |
| Ser | Ser | Lys | Pro | Pro | Thr | Phe | Gly | Gly | Gly | Thr | Lys | Leu | Glu | Ile | Lys | |
| | | 115 | | | | | 120 | | | | | 125 | | | | |
| CGG | | | | | | | | | | | | | | | | 387 |
| Arg | | | | | | | | | | | | | | | | |

( 2 ) INFORMATION FOR SEQ ID NO:2:

( i ) SEQUENCE CHARACTERISTICS:
        ( A ) LENGTH: 129 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | | |
|---|---|---|---|---|---|---|---|---|---|---|---|---|---|---|---|
| Met | Asp | Phe | Gln | Val | Gln | Ile | Phe | Ser | Phe | Leu | Leu | Ile | Ser | Ala | Ser |
| 1 | | | | 5 | | | | | 10 | | | | | 15 | |
| Val | Ile | Met | Ser | Arg | Gly | Gln | Thr | Val | Leu | Ser | Gln | Ser | Pro | Ala | Ile |
| | | | 20 | | | | | 25 | | | | | 30 | | |
| Leu | Ser | Ala | Ser | Pro | Gly | Glu | Lys | Val | Thr | Met | Thr | Cys | Arg | Ala | Ser |
| | | | 35 | | | | | 40 | | | | | 45 | | |
| Ser | Ser | Val | Thr | Tyr | Ile | His | Trp | Tyr | Gln | Gln | Lys | Pro | Gly | Ser | Ser |
| | 50 | | | | 55 | | | | | 60 | | | | | |
| Pro | Lys | Ser | Trp | Ile | Tyr | Ala | Thr | Ser | Asn | Leu | Ala | Ser | Gly | Val | Pro |
| 65 | | | | 70 | | | | | 75 | | | | | 80 | |
| Ala | Arg | Phe | Ser | Gly | Ser | Gly | Ser | Gly | Thr | Ser | Tyr | Ser | Leu | Thr | Ile |
| | | | | 85 | | | | | 90 | | | | | 95 | |
| Ser | Arg | Val | Glu | Ala | Glu | Asp | Ala | Ala | Thr | Tyr | Tyr | Cys | Gln | His | Trp |
| | | | 100 | | | | | 105 | | | | | 110 | | |
| Ser | Ser | Lys | Pro | Pro | Thr | Phe | Gly | Gly | Gly | Thr | Lys | Leu | Glu | Ile | Lys |
| | | 115 | | | | | 120 | | | | | 125 | | | |
| Arg | | | | | | | | | | | | | | | |

( 2 ) INFORMATION FOR SEQ ID NO:3:

( i ) SEQUENCE CHARACTERISTICS:
        ( A ) LENGTH: 420 base pairs
        ( B ) TYPE: nucleic acid
        ( C ) STRANDEDNESS: double
        ( D ) TOPOLOGY: linear ( v i i ) IMMEDIATE SOURCE:
        ( B ) CLONE: A5B7 heavy chain Vh domain ( i x ) FEATURE:
        ( A ) NAME/KEY: CDS
        ( B ) LOCATION: 1..420

( x i ) SEQUENCE DESCRIPTION: SEQ ID NO:3:

| | | | | | | | | | | | | | | | | |
|---|---|---|---|---|---|---|---|---|---|---|---|---|---|---|---|---|
| ATG | AAG | TTG | TGG | CTG | AAC | TGG | ATT | TTC | CTT | GTA | ACA | CTT | TTA | AAT | GGT | 48 |

|     |     |     |     |     |     |     |     |     |     |     |     |     |     |     |     |     |
|---|---|---|---|---|---|---|---|---|---|---|---|---|---|---|---|---|
| Met | Lys | Leu | Trp | Leu | Asn | Trp | Ile | Phe | Leu | Val | Thr | Leu | Leu | Asn | Gly |  |
| 1   |     |     |     | 5   |     |     |     |     | 10  |     |     |     |     | 15  |     |  |
| ATC | CAG | TGT | GAG | GTG | AAG | CTG | GTG | GAG | TCT | GGA | GGA | GGC | TTG | GTA | CAG | 96 |
| Ile | Gln | Cys | Glu | Val | Lys | Leu | Val | Glu | Ser | Gly | Gly | Gly | Leu | Val | Gln |  |
|     |     |     | 20  |     |     |     |     | 25  |     |     |     |     | 30  |     |     |  |
| CCT | GGG | GGT | TCT | CTG | AGA | CTC | TCC | TGT | GCA | ACT | TCT | GGG | TTC | ACC | TTC | 144 |
| Pro | Gly | Gly | Ser | Leu | Arg | Leu | Ser | Cys | Ala | Thr | Ser | Gly | Phe | Thr | Phe |  |
|     |     | 35  |     |     |     |     | 40  |     |     |     |     | 45  |     |     |     |  |
| ACT | GAT | TAC | TAC | ATG | AAC | TGG | GTC | CGC | CAG | CCT | CCA | GGA | AAG | GCA | CTT | 192 |
| Thr | Asp | Tyr | Tyr | Met | Asn | Trp | Val | Arg | Gln | Pro | Pro | Gly | Lys | Ala | Leu |  |
|     | 50  |     |     |     |     | 55  |     |     |     |     | 60  |     |     |     |     |  |
| GAG | TGG | TTG | GGT | TTT | ATT | GGA | AAC | AAA | GCT | AAT | GGT | TAC | ACA | ACA | GAG | 240 |
| Glu | Trp | Leu | Gly | Phe | Ile | Gly | Asn | Lys | Ala | Asn | Gly | Tyr | Thr | Thr | Glu |  |
| 65  |     |     |     |     | 70  |     |     |     |     | 75  |     |     |     |     | 80  |  |
| TAC | AGT | GCA | TCT | GTG | AAG | GGT | CGG | TTC | ACC | ATC | TCC | AGA | GAT | AAA | TCC | 288 |
| Tyr | Ser | Ala | Ser | Val | Lys | Gly | Arg | Phe | Thr | Ile | Ser | Arg | Asp | Lys | Ser |  |
|     |     |     |     | 85  |     |     |     |     | 90  |     |     |     |     | 95  |     |  |
| CAA | AGC | ATC | CTC | TAT | CTT | CAA | ATG | AAC | ACC | CTG | AGA | GCT | GAG | GAC | AGT | 336 |
| Gln | Ser | Ile | Leu | Tyr | Leu | Gln | Met | Asn | Thr | Leu | Arg | Ala | Glu | Asp | Ser |  |
|     |     |     | 100 |     |     |     |     | 105 |     |     |     |     | 110 |     |     |  |
| GCC | ACT | TAT | TAC | TGT | ACA | AGA | GAT | AGG | GGG | CTA | CGG | TTC | TAC | TTT | GAC | 384 |
| Ala | Thr | Tyr | Tyr | Cys | Thr | Arg | Asp | Arg | Gly | Leu | Arg | Phe | Tyr | Phe | Asp |  |
|     |     | 115 |     |     |     |     | 120 |     |     |     |     | 125 |     |     |     |  |
| TAC | TGG | GGC | CAA | GGC | ACC | ACT | CTC | ACA | GTC | TCC | TCA |     |     |     |     | 420 |
| Tyr | Trp | Gly | Gln | Gly | Thr | Thr | Leu | Thr | Val | Ser | Ser |     |     |     |     |  |
|     | 130 |     |     |     |     | 135 |     |     |     |     | 140 |     |     |     |     |  |

( 2 ) INFORMATION FOR SEQ ID NO:4:

( i ) SEQUENCE CHARACTERISTICS:
( A ) LENGTH: 140 amino acids
( B ) TYPE: amino acid
( D ) TOPOLOGY: linear ( i i ) MOLECULE TYPE: protein ( x i ) SEQUENCE DESCRIPTION: SEQ ID NO:4:

|     |     |     |     |     |     |     |     |     |     |     |     |     |     |     |     |
|---|---|---|---|---|---|---|---|---|---|---|---|---|---|---|---|
| Met | Lys | Leu | Trp | Leu | Asn | Trp | Ile | Phe | Leu | Val | Thr | Leu | Leu | Asn | Gly |
| 1   |     |     |     | 5   |     |     |     |     | 10  |     |     |     |     | 15  |     |
| Ile | Gln | Cys | Glu | Val | Lys | Leu | Val | Glu | Ser | Gly | Gly | Gly | Leu | Val | Gln |
|     |     |     | 20  |     |     |     |     | 25  |     |     |     |     | 30  |     |     |
| Pro | Gly | Gly | Ser | Leu | Arg | Leu | Ser | Cys | Ala | Thr | Ser | Gly | Phe | Thr | Phe |
|     |     | 35  |     |     |     |     | 40  |     |     |     |     | 45  |     |     |     |
| Thr | Asp | Tyr | Tyr | Met | Asn | Trp | Val | Arg | Gln | Pro | Pro | Gly | Lys | Ala | Leu |
|     | 50  |     |     |     |     | 55  |     |     |     |     | 60  |     |     |     |     |
| Glu | Trp | Leu | Gly | Phe | Ile | Gly | Asn | Lys | Ala | Asn | Gly | Tyr | Thr | Thr | Glu |
| 65  |     |     |     |     | 70  |     |     |     |     | 75  |     |     |     |     | 80  |
| Tyr | Ser | Ala | Ser | Val | Lys | Gly | Arg | Phe | Thr | Ile | Ser | Arg | Asp | Lys | Ser |
|     |     |     |     | 85  |     |     |     |     | 90  |     |     |     |     | 95  |     |
| Gln | Ser | Ile | Leu | Tyr | Leu | Gln | Met | Asn | Thr | Leu | Arg | Ala | Glu | Asp | Ser |
|     |     |     | 100 |     |     |     |     | 105 |     |     |     |     | 110 |     |     |
| Ala | Thr | Tyr | Tyr | Cys | Thr | Arg | Asp | Arg | Gly | Leu | Arg | Phe | Tyr | Phe | Asp |
|     |     | 115 |     |     |     |     | 120 |     |     |     |     | 125 |     |     |     |
| Tyr | Trp | Gly | Gln | Gly | Thr | Thr | Leu | Thr | Val | Ser | Ser |     |     |     |     |
|     | 130 |     |     |     |     | 135 |     |     |     |     | 140 |     |     |     |     |

( 2 ) INFORMATION FOR SEQ ID NO:5:

( i ) SEQUENCE CHARACTERISTICS:
( A ) LENGTH: 411 base pairs
( B ) TYPE: nucleic acid ( C ) STRANDEDNESS: double
( D ) TOPOLOGY: linear ( v i i ) IMMEDIATE SOURCE:
( B ) CLONE: gL1-A5B7 variable region ( i x ) FEATURE:
( A ) NAME/KEY: CDS
( B ) LOCATION: 22..405

( x i ) SEQUENCE DESCRIPTION: SEQ ID NO:5:

```
GGACTGTTCG AAGCCGCCAC C ATG TCT GTC CCC ACC CAA GTC CTC GGA CTC       51
                         Met Ser Val Pro Thr Gln Val Leu Gly Leu
                          1               5                    10

CTG CTG CTG TGG CTT ACA GAT GCC AGA TGT CAG ACT GTA CTC ACT CAG       99
Leu Leu Leu Trp Leu Thr Asp Ala Arg Cys Gln Thr Val Leu Thr Gln
             15                  20                      25

AGT CCA AGT AGT CTC AGT GTA AGT GTA GGT GAT AGG GTA ACT ATC ACT      147
Ser Pro Ser Ser Leu Ser Val Ser Val Gly Asp Arg Val Thr Ile Thr
             30                  35                      40

TGT AGG GCC AGT AGT AGT GTA ACT TAT ATC CAT TGG TAT CAG CAG AAA      195
Cys Arg Ala Ser Ser Ser Val Thr Tyr Ile His Trp Tyr Gln Gln Lys
             45              50                  55

CCA GGT CTC GCC CCA AAA AGT CTC ATC TAT GCC ACT AGT AAC CTC GCC      243
Pro Gly Leu Ala Pro Lys Ser Leu Ile Tyr Ala Thr Ser Asn Leu Ala
         60              65                  70

AGT GGT GTA CCA TCT AGA TTC AGT GGT AGC GGT AGT GGT ACT GAT TAT      291
Ser Gly Val Pro Ser Arg Phe Ser Gly Ser Gly Ser Gly Thr Asp Tyr
 75                  80                  85                  90

ACT TTC ACT ATC AGT AGT CTC CAG CCA GAA GAT ATC GCC ACT TAC TAT      339
Thr Phe Thr Ile Ser Ser Leu Gln Pro Glu Asp Ile Ala Thr Tyr Tyr
                 95                 100                 105

TGC CAG CAT TGG AGT AGT AAA CCA CCA ACT TTC GGT CAG GGT ACT AAA      387
Cys Gln His Trp Ser Ser Lys Pro Pro Thr Phe Gly Gln Gly Thr Lys
             110                 115                 120

GTA GAA GTA AAA CGT ACG GGCCGG                                        411
Val Glu Val Lys Arg Thr
             125
```

( 2 ) INFORMATION FOR SEQ ID NO:6:

( i ) SEQUENCE CHARACTERISTICS:
( A ) LENGTH: 128 amino acids
( B ) TYPE: amino acid
( D ) TOPOLOGY: linear ( i i ) MOLECULE TYPE: protein ( x i ) SEQUENCE DESCRIPTION: SEQ ID NO:6:

```
Met Ser Val Pro Thr Gln Val Leu Gly Leu Leu Leu Leu Trp Leu Thr
 1               5                  10                      15

Asp Ala Arg Cys Gln Thr Val Leu Thr Gln Ser Pro Ser Ser Leu Ser
             20                  25                      30

Val Ser Val Gly Asp Arg Val Thr Ile Thr Cys Arg Ala Ser Ser Ser
             35                  40                      45

Val Thr Tyr Ile His Trp Tyr Gln Gln Lys Pro Gly Leu Ala Pro Lys
         50                  55                  60

Ser Leu Ile Tyr Ala Thr Ser Asn Leu Ala Ser Gly Val Pro Ser Arg
 65                  70                  75                  80

Phe Ser Gly Ser Gly Ser Gly Thr Asp Tyr Thr Phe Thr Ile Ser Ser
                 85                  90                  95

Leu Gln Pro Glu Asp Ile Ala Thr Tyr Tyr Cys Gln His Trp Ser Ser
             100                 105                 110
```

```
Lys  Pro  Pro  Thr  Phe  Gly  Gln  Gly  Thr  Lys  Val  Glu  Val  Lys  Arg  Thr
          115                 120                      125
```

( 2 ) INFORMATION FOR SEQ ID NO:7:

( i ) SEQUENCE CHARACTERISTICS:
        ( A ) LENGTH: 411 base pairs
        ( B ) TYPE: nucleic acid
        ( C ) STRANDEDNESS: double
        ( D ) TOPOLOGY: linear ( v i i ) IMMEDIATE SOURCE:
        ( B ) CLONE: gL2-A5B7 variable region ( i x ) FEATURE:
        ( A ) NAME/KEY: CDS
        ( B ) LOCATION: 22..405

( x i ) SEQUENCE DESCRIPTION: SEQ ID NO:7:

```
GGACTGTTCG  AAGCCGCCAC  C  ATG  TCT  GTC  CCC  ACC  CAA  GTC  CTC  GGA  CTC        51
                           Met  Ser  Val  Pro  Thr  Gln  Val  Leu  Gly  Leu
                            1              5                            10

CTG  CTG  CTG  TGG  CTT  ACA  GAT  GCC  AGA  TGT  CAG  ACT  GTA  CTC  ACT  CAG    99
Leu  Leu  Leu  Trp  Leu  Thr  Asp  Ala  Arg  Cys  Gln  Thr  Val  Leu  Thr  Gln
               15                         20                           25

AGT  CCA  AGT  AGT  CTC  AGT  GTA  AGT  GTA  GGT  GAT  AGG  GTA  ACT  ATG  ACT   147
Ser  Pro  Ser  Ser  Leu  Ser  Val  Ser  Val  Gly  Asp  Arg  Val  Thr  Met  Thr
               30                         35                           40

TGT  AGG  GCC  AGT  AGT  AGT  GTA  ACT  TAT  ATC  CAT  TGG  TAT  CAG  CAG  AAA   195
Cys  Arg  Ala  Ser  Ser  Ser  Val  Thr  Tyr  Ile  His  Trp  Tyr  Gln  Gln  Lys
               45                         50                           55

CCA  GGT  CTC  GCC  CCA  AAA  AGT  TGG  ATC  TAT  GCC  ACT  AGT  AAC  CTC  GCC   243
Pro  Gly  Leu  Ala  Pro  Lys  Ser  Trp  Ile  Tyr  Ala  Thr  Ser  Asn  Leu  Ala
          60                  65                      70

AGT  GGT  GTA  CCA  TCT  AGA  TTC  AGT  GGT  AGC  GGT  AGT  GGT  ACT  GAT  TAT   291
Ser  Gly  Val  Pro  Ser  Arg  Phe  Ser  Gly  Ser  Gly  Ser  Gly  Thr  Asp  Tyr
75                       80                       85                       90

ACT  CTC  ACT  ATC  AGT  AGT  CTC  CAG  CCA  GAA  GAT  ATC  GCC  ACT  TAC  TAT   339
Thr  Leu  Thr  Ile  Ser  Ser  Leu  Gln  Pro  Glu  Asp  Ile  Ala  Thr  Tyr  Tyr
               95                         100                          105

TGC  CAG  CAT  TGG  AGT  AGT  AAA  CCA  CCA  ACT  TTC  GGT  CAG  GGT  ACT  AAA   387
Cys  Gln  His  Trp  Ser  Ser  Lys  Pro  Pro  Thr  Phe  Gly  Gln  Gly  Thr  Lys
          110                 115                     120

GTA  GAA  GTA  AAA  CGT  ACG  GGCCGG                                              411
Val  Glu  Val  Lys  Arg  Thr
          125
```

( 2 ) INFORMATION FOR SEQ ID NO:8:

( i ) SEQUENCE CHARACTERISTICS:
        ( A ) LENGTH: 128 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met  Ser  Val  Pro  Thr  Gln  Val  Leu  Gly  Leu  Leu  Leu  Leu  Trp  Leu  Thr
 1              5                        10                            15

Asp  Ala  Arg  Cys  Gln  Thr  Val  Leu  Thr  Gln  Ser  Pro  Ser  Ser  Leu  Ser
               20                      25                      30

Val  Ser  Val  Gly  Asp  Arg  Val  Thr  Met  Thr  Cys  Arg  Ala  Ser  Ser  Ser
          35                       40                      45

Val  Thr  Tyr  Ile  His  Trp  Tyr  Gln  Gln  Lys  Pro  Gly  Leu  Ala  Pro  Lys
```

```
              50                       55                         60
Ser  Trp  Ile  Tyr  Ala  Thr  Ser  Asn  Leu  Ala  Ser  Gly  Val  Pro  Ser  Arg
 65                      70                      75                       80

Phe  Ser  Gly  Ser  Gly  Ser  Gly  Thr  Asp  Tyr  Thr  Leu  Thr  Ile  Ser  Ser
                85                        90                       95

Leu  Gln  Pro  Glu  Asp  Ile  Ala  Thr  Tyr  Tyr  Cys  Gln  His  Trp  Ser  Ser
               100                       105                      110

Lys  Pro  Pro  Thr  Phe  Gly  Gln  Gly  Thr  Lys  Val  Glu  Val  Lys  Arg  Thr
               115                       120                      125
```

( 2 ) INFORMATION FOR SEQ ID NO:9:

( i ) SEQUENCE CHARACTERISTICS:
        ( A ) LENGTH: 464 base pairs
        ( B ) TYPE: nucleic acid
        ( C ) STRANDEDNESS: double
        ( D ) TOPOLOGY: linear ( v i i ) IMMEDIATE SOURCE:
        ( B ) CLONE: gH1-A5B7 variable region ( i x ) FEATURE:
        ( A ) NAME/KEY: CDS
        ( B ) LOCATION: 22..459

( x i ) SEQUENCE DESCRIPTION: SEQ ID NO:9:

```
GCGCGCAAGC  TTGCCGCCAC  C  ATG  GAA  TGG  AGC  TGG  GTC  TTT  CTC  TTC  TTC     51
                           Met  Glu  Trp  Ser  Trp  Val  Phe  Leu  Phe  Phe
                            1                   5                       10

CTG  TCA  GTA  ACT  ACA  GGA  GTC  CAT  TCT  GAG  GTG  CAG  CTG  CTG  GAG  TCT   99
Leu  Ser  Val  Thr  Thr  Gly  Val  His  Ser  Glu  Val  Gln  Leu  Leu  Glu  Ser
                    15                       20                       25

GGA  GGA  GGA  CTG  GTG  CAG  CCT  GGA  GGA  TCT  CTG  AGA  CTG  TCT  TGT  GCA  147
Gly  Gly  Gly  Leu  Val  Gln  Pro  Gly  Gly  Ser  Leu  Arg  Leu  Ser  Cys  Ala
               30                       35                       40

ACA  TCT  GGA  TTC  ACC  TTC  ACA  GAC  TAC  TAC  ATG  AAT  TGG  GTG  AGA  CAG  195
Thr  Ser  Gly  Phe  Thr  Phe  Thr  Asp  Tyr  Tyr  Met  Asn  Trp  Val  Arg  Gln
               45                       50                       55

GCA  CCT  GGA  AAG  GGA  CTC  GAG  TGG  CTG  GGC  TTC  ATC  GGA  AAT  AAG  GCA  243
Ala  Pro  Gly  Lys  Gly  Leu  Glu  Trp  Leu  Gly  Phe  Ile  Gly  Asn  Lys  Ala
          60                       65                       70

AAT  GGA  TAC  ACA  ACA  GAG  TAC  TCT  GCA  TCT  GTG  AAG  GGA  AGA  TTC  ACA  291
Asn  Gly  Tyr  Thr  Thr  Glu  Tyr  Ser  Ala  Ser  Val  Lys  Gly  Arg  Phe  Thr
 75                      80                       85                       90

ATT  TCC  AGA  GAC  AAG  AGC  AAG  TCC  ACA  CTG  TAC  CTG  CAG  ATG  AAT  GGA  339
Ile  Ser  Arg  Asp  Lys  Ser  Lys  Ser  Thr  Leu  Tyr  Leu  Gln  Met  Asn  Gly
                    95                       100                     105

CTG  CAG  GCA  GAG  GTG  TCT  GCA  ATT  TAC  TAC  TGT  ACA  AGA  GAC  AGA  GGA  387
Leu  Gln  Ala  Glu  Val  Ser  Ala  Ile  Tyr  Tyr  Cys  Thr  Arg  Asp  Arg  Gly
               110                      115                      120

CTG  AGA  TTC  TAC  TTC  GAC  TAC  TGG  GGA  CAG  GGA  ACA  CTG  GTG  ACA  GTG  435
Leu  Arg  Phe  Tyr  Phe  Asp  Tyr  Trp  Gly  Gln  Gly  Thr  Leu  Val  Thr  Val
               125                      130                      135

TCT  TCT  GCC  TCA  ACG  AAG  GGC  CCG  CGCGC                                   464
Ser  Ser  Ala  Ser  Thr  Lys  Gly  Pro
 140                     145
```

( 2 ) INFORMATION FOR SEQ ID NO:10:

( i ) SEQUENCE CHARACTERISTICS:
        ( A ) LENGTH: 146 amino acids
        ( B ) TYPE: amino acid
        ( D ) TOPOLOGY: linear (i i) MOLECULE TYPE: protein (x i) SEQUENCE DESCRIPTION: SEQ ID NO:10:

| Met | Glu | Trp | Ser | Trp | Val | Phe | Leu | Phe | Phe | Leu | Ser | Val | Thr | Thr | Gly |
|---|---|---|---|---|---|---|---|---|---|---|---|---|---|---|---|
| 1 | | | | 5 | | | | | 10 | | | | | 15 | |
| Val | His | Ser | Glu | Val | Gln | Leu | Leu | Glu | Ser | Gly | Gly | Gly | Leu | Val | Gln |
| | | | 20 | | | | | 25 | | | | | 30 | | |
| Pro | Gly | Gly | Ser | Leu | Arg | Leu | Ser | Cys | Ala | Thr | Ser | Gly | Phe | Thr | Phe |
| | | 35 | | | | | 40 | | | | | 45 | | | |
| Thr | Asp | Tyr | Tyr | Met | Asn | Trp | Val | Arg | Gln | Ala | Pro | Gly | Lys | Gly | Leu |
| | 50 | | | | | 55 | | | | | 60 | | | | |
| Glu | Trp | Leu | Gly | Phe | Ile | Gly | Asn | Lys | Ala | Asn | Gly | Tyr | Thr | Thr | Glu |
| 65 | | | | | 70 | | | | | 75 | | | | | 80 |
| Tyr | Ser | Ala | Ser | Val | Lys | Gly | Arg | Phe | Thr | Ile | Ser | Arg | Asp | Lys | Ser |
| | | | | 85 | | | | | 90 | | | | | 95 | |
| Lys | Ser | Thr | Leu | Tyr | Leu | Gln | Met | Asn | Gly | Leu | Gln | Ala | Glu | Val | Ser |
| | | | 100 | | | | | 105 | | | | | 110 | | |
| Ala | Ile | Tyr | Tyr | Cys | Thr | Arg | Asp | Arg | Gly | Leu | Arg | Phe | Tyr | Phe | Asp |
| | | 115 | | | | | 120 | | | | | 125 | | | |
| Tyr | Trp | Gly | Gln | Gly | Thr | Leu | Val | Thr | Val | Ser | Ser | Ala | Ser | Thr | Lys |
| | 130 | | | | | 135 | | | | | 140 | | | | |
| Gly | Pro | | | | | | | | | | | | | | |
| 145 | | | | | | | | | | | | | | | |

(2) INFORMATION FOR SEQ ID NO:11:

(i) SEQUENCE CHARACTERISTICS:
(A) LENGTH: 464 base pairs
(B) TYPE: nucleic acid
(C) STRANDEDNESS: double
(D) TOPOLOGY: linear (v i i) IMMEDIATE SOURCE:
(B) CLONE: gH2-A5B7 variable region (i x) FEATURE:
(A) NAME/KEY: CDS
(B) LOCATION: 22..459

(x i) SEQUENCE DESCRIPTION: SEQ ID NO:11:

| GCGCGCAAGC | TTGCCGCCAC | C | ATG | GAA | TGG | AGC | TGG | GTC | TTT | CTC | TTC | TTC | 51 |
|---|---|---|---|---|---|---|---|---|---|---|---|---|---|
| | | | Met | Glu | Trp | Ser | Trp | Val | Phe | Leu | Phe | Phe | |
| | | | 1 | | | | 5 | | | | | 10 | |

| CTG | TCA | GTA | ACT | ACA | GGA | GTC | CAT | TCT | GAG | GTG | CAG | CTG | CTG | GAG | TCT | 99 |
|---|---|---|---|---|---|---|---|---|---|---|---|---|---|---|---|---|
| Leu | Ser | Val | Thr | Thr | Gly | Val | His | Ser | Glu | Val | Gln | Leu | Leu | Glu | Ser | |
| | | | | 15 | | | | | 20 | | | | | 25 | | |

| GGA | GGA | GGA | CTG | GTG | CAG | CCT | GGA | GGA | TCT | CTG | AGA | CTG | TCT | TGT | GCA | 147 |
|---|---|---|---|---|---|---|---|---|---|---|---|---|---|---|---|---|
| Gly | Gly | Gly | Leu | Val | Gln | Pro | Gly | Gly | Ser | Leu | Arg | Leu | Ser | Cys | Ala | |
| | | | 30 | | | | | 35 | | | | | 40 | | | |

| ACA | TCT | GGA | TTC | ACC | TTC | ACA | GAC | TAC | TAC | ATG | AAT | TGG | GTG | AGA | CAG | 195 |
|---|---|---|---|---|---|---|---|---|---|---|---|---|---|---|---|---|
| Thr | Ser | Gly | Phe | Thr | Phe | Thr | Asp | Tyr | Tyr | Met | Asn | Trp | Val | Arg | Gln | |
| | | | 45 | | | | | 50 | | | | | 55 | | | |

| GCA | CCT | GGA | AAG | GGA | CTC | GAG | TGG | CTG | GGC | TTC | ATC | GGA | AAT | AAG | GCA | 243 |
|---|---|---|---|---|---|---|---|---|---|---|---|---|---|---|---|---|
| Ala | Pro | Gly | Lys | Gly | Leu | Glu | Trp | Leu | Gly | Phe | Ile | Gly | Asn | Lys | Ala | |
| | | 60 | | | | | 65 | | | | | 70 | | | | |

| AAT | GGA | TAC | ACA | ACA | GAG | TAC | TCT | GCA | TCT | GTG | AAG | GGA | AGA | TTC | ACA | 291 |
|---|---|---|---|---|---|---|---|---|---|---|---|---|---|---|---|---|
| Asn | Gly | Tyr | Thr | Thr | Glu | Tyr | Ser | Ala | Ser | Val | Lys | Gly | Arg | Phe | Thr | |
| 75 | | | | | 80 | | | | | 85 | | | | | 90 | |

| ATT | TCC | AGA | GAC | AAG | AGC | AAG | TCC | ACA | CTG | TAC | CTG | CAG | ATG | AAT | ACA | 339 |
|---|---|---|---|---|---|---|---|---|---|---|---|---|---|---|---|---|
| Ile | Ser | Arg | Asp | Lys | Ser | Lys | Ser | Thr | Leu | Tyr | Leu | Gln | Met | Asn | Thr | |
| | | | | 95 | | | | | 100 | | | | | 105 | | |

```
CTG  CAG  GCA  GAG  GAC  TCT  GCA  ATT  TAC  TAC  TGT  ACA  AGA  GAC  AGA  GGA        387
Leu  Gln  Ala  Glu  Asp  Ser  Ala  Ile  Tyr  Tyr  Cys  Thr  Arg  Asp  Arg  Gly
               110                      115                     120

CTG  AGA  TTC  TAC  TTC  GAC  TAC  TGG  GGA  CAG  GGA  ACA  CTG  GTG  ACA  GTG        435
Leu  Arg  Phe  Tyr  Phe  Asp  Tyr  Trp  Gly  Gln  Gly  Thr  Leu  Val  Thr  Val
          125                      130                     135

TCT  TCT  GCC  TCA  ACG  AAG  GGC  CCG  CGCGC                                          464
Ser  Ser  Ala  Ser  Thr  Lys  Gly  Pro
140                           145
```

( 2 ) INFORMATION FOR SEQ ID NO:12:

( i ) SEQUENCE CHARACTERISTICS:
        ( A ) LENGTH: 146 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Met  Glu  Trp  Ser  Trp  Val  Phe  Leu  Phe  Phe  Leu  Ser  Val  Thr  Thr  Gly
1                    5                     10                    15

Val  His  Ser  Glu  Val  Gln  Leu  Leu  Glu  Ser  Gly  Gly  Gly  Leu  Val  Gln
               20                     25                    30

Pro  Gly  Gly  Ser  Leu  Arg  Leu  Ser  Cys  Ala  Thr  Ser  Gly  Phe  Thr  Phe
          35                     40                    45

Thr  Asp  Tyr  Tyr  Met  Asn  Trp  Val  Arg  Gln  Ala  Pro  Gly  Lys  Gly  Leu
     50                     55                    60

Glu  Trp  Leu  Gly  Phe  Ile  Gly  Asn  Lys  Ala  Asn  Gly  Tyr  Thr  Thr  Glu
65                        70                    75                         80

Tyr  Ser  Ala  Ser  Val  Lys  Gly  Arg  Phe  Thr  Ile  Ser  Arg  Asp  Lys  Ser
                    85                     90                         95

Lys  Ser  Thr  Leu  Tyr  Leu  Gln  Met  Asn  Thr  Leu  Gln  Ala  Glu  Asp  Ser
               100                     105                    110

Ala  Ile  Tyr  Tyr  Cys  Thr  Arg  Asp  Arg  Gly  Leu  Arg  Phe  Tyr  Phe  Asp
          115                     120                     125

Tyr  Trp  Gly  Gln  Gly  Thr  Leu  Val  Thr  Val  Ser  Ser  Ala  Ser  Thr  Lys
     130                     135                    140

Gly  Pro
145
```

( 2 ) INFORMATION FOR SEQ ID NO:13:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: R1120

( x i ) SEQUENCE DESCRIPTION: SEQ ID NO:13:

```
GCACCACTCT  CACCGTGAGC  TC                                                              22
```

( 2 ) INFORMATION FOR SEQ ID NO:14:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i v ) ANTI-SENSE: YES (v i i) IMMEDIATE SOURCE:
  (B) CLONE: R1121

(x i) SEQUENCE DESCRIPTION: SEQ ID NO:14:

AGCTGAGCTC ACGGTGAGAG TG                              22

(2) INFORMATION FOR SEQ ID NO:15:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (x i) SEQUENCE DESCRIPTION: SEQ ID NO:15:

TTTGATTTCA AGCTTGGTGC                                 20

(2) INFORMATION FOR SEQ ID NO:16:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (v i i) IMMEDIATE SOURCE:
    (B) CLONE: R1053

(x i) SEQUENCE DESCRIPTION: SEQ ID NO:16:

GTCGACAGAC TAACAGACTG TTCC                            24

(2) INFORMATION FOR SEQ ID NO:17:

(i) SEQUENCE CHARACTERISTICS:
    (A) LENGTH: 54 base pairs
    (B) TYPE: nucleic acid
    (C) STRANDEDNESS: single
    (D) TOPOLOGY: linear (v i i) IMMEDIATE SOURCE:
    (B) CLONE: R2371

(x i) SEQUENCE DESCRIPTION: SEQ ID NO:17:

ATGATCAATG AATTCATCAT GGGGCTGATG GGCACGGGGA CCATATTTGG ACTC     54

(2) INFORMATION FOR SEQ ID NO:18:

(i) SEQUENCE CHARACTERISTICS:
    (A) LENGTH: 87 base pairs
    (B) TYPE: nucleic acid
    (C) STRANDEDNESS: single
    (D) TOPOLOGY: linear (x i) SEQUENCE DESCRIPTION: SEQ ID NO:18:

TCGAGTTCTA GATAACGAGG CGTAAAAAAT GAAAAAGACA GCTATCGCGA TTGCAGTGGC     60

ACTGGCTGGT TTCGCTACCG TAGCGCA                                         87

(2) INFORMATION FOR SEQ ID NO:19:

(i) SEQUENCE CHARACTERISTICS:
    (A) LENGTH: 87 base pairs
    (B) TYPE: nucleic acid
    (C) STRANDEDNESS: single
    (D) TOPOLOGY: linear (i v) ANTI-SENSE: YES (x i) SEQUENCE DESCRIPTION: SEQ ID NO:19:

```
AGCTTGCGCT ACGGTAGCGA AACCAGCCAG TGCCACTGCA ATCGCGATAG CTGTCTTTTT          60

CATTTTTTAC GCCTCGTTAT CTAGAAC                                              87
```

( 2 ) INFORMATION FOR SEQ ID NO:20:

( i ) SEQUENCE CHARACTERISTICS:
    ( A ) LENGTH: 21 amino acids
    ( B ) TYPE: amino acid
    ( D ) TOPOLOGY: linear ( x i ) SEQUENCE DESCRIPTION: SEQ ID NO:20:

```
Met Lys Lys Thr Ala Ile Ala Ile Ala Val Ala Leu Ala Gly Phe Ala
 1               5                  10                  15

Thr Val Ala Gln Ala
            20
```

( 2 ) INFORMATION FOR SEQ ID NO:21:

( i ) SEQUENCE CHARACTERISTICS:
    ( A ) LENGTH: 46 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:21:

```
AGCTCAAACT GTTCTCTCCC AGTCTCCAGC AATCTGTCTG CATCTC                         46
```

( 2 ) INFORMATION FOR SEQ ID NO:22:

( i ) SEQUENCE CHARACTERISTICS:
    ( A ) LENGTH: 47 base pairs
    ( B ) TYPE: nucleic acid
    ( C ) STRANDEDNESS: single
    ( D ) TOPOLOGY: linear ( i v ) ANTI-SENSE: YES ( x i ) SEQUENCE DESCRIPTION: SEQ ID NO:22:

```
CCTGGAGATG CAGACAGGAT TGCTGGAGAC TGGGAGAGAA CAGTTTG                        47
```

( 2 ) INFORMATION FOR SEQ ID NO:23:

( i ) SEQUENCE CHARACTERISTICS:
    ( A ) LENGTH: 112 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:23:

```
AGCTGAGGTG AAGCTTGTGG AGTCTGGAGG AGGGTTGGTA CAGCCTGGGG GTTCTCTGAG          60

ACTCTCCTGT GCAACTTCTG GGTTCACCTT CACTGATTAC TACATGAACT GG                 112
```

( 2 ) INFORMATION FOR SEQ ID NO:24:

( i ) SEQUENCE CHARACTERISTICS:
    ( A ) LENGTH: 112 base pairs
    ( B ) TYPE: nucleic acid
    ( C ) STRANDEDNESS: single
    ( D ) TOPOLOGY: linear ( i v ) ANTI-SENSE: YES ( x i ) SEQUENCE DESCRIPTION: SEQ ID NO:24:

```
GGACCCAGTT CATGTAGTAA TCAGTGAAGG TGAACCCAGA AGTTGCACAG GAGAGTCTCA          60

GAGAACCCCC AGGCTGTACC AAGCCTCCTC CAGACTCCAC AAGCTTCACC TC                 112
```

(2) INFORMATION FOR SEQ ID NO:25:

(i) SEQUENCE CHARACTERISTICS:
       (A) LENGTH: 62 base pairs
       (B) TYPE: nucleic acid
       (C) STRANDEDNESS: single
       (D) TOPOLOGY: linear (xi) SEQUENCE DESCRIPTION: SEQ ID NO:25:

AGCTCAGACT GTACTCACTC AGAGTCCAAG TAGTCTCAGT GTAAGTGTAG GTGATAGGGT            60

AA                                                                          62

(2) INFORMATION FOR SEQ ID NO:26:

(i) SEQUENCE CHARACTERISTICS:
       (A) LENGTH: 57 base pairs
       (B) TYPE: nucleic acid
       (C) STRANDEDNESS: single
       (D) TOPOLOGY: linear (iv) ANTI-SENSE: YES (xi) SEQUENCE DESCRIPTION: SEQ ID NO:26:

TACCCTATCA CCTACACTTA CACTGAGACT ACTTGGACTC TGAGTGAGTA CAGTCTG             57

(2) INFORMATION FOR SEQ ID NO:27:

(i) SEQUENCE CHARACTERISTICS:
       (A) LENGTH: 13 base pairs
       (B) TYPE: nucleic acid
       (C) STRANDEDNESS: single
       (D) TOPOLOGY: linear (xi) SEQUENCE DESCRIPTION: SEQ ID NO:27:

AGCTGAGGTG CAG                                                              13